(12) United States Patent
Gould et al.

(10) Patent No.: US 12,744,125 B2
(45) Date of Patent: Sep. 22, 2026

(54) PERSONAL PROFILE GENERATOR AND RECOMMENDATION ENGINE

(71) Applicant: Kenvue Brands LLC, Summit, NJ (US)

(72) Inventors: Russell Gould, Washington Crossing, PA (US); Soyoun Kristin Chung, Brooklyn, NY (US); Benjamin Serbiak, Georgetown, TX (US); Bryan Patrick Cunningham, Bridgewater, NJ (US); Jingting Zhang, Toronto (CA)

(73) Assignee: Kenvue Brands LLC, Summit, NJ (US)

( * ) Notice: Subject to any disclaimer, the term of this patent is extended or adjusted under 35 U.S.C. 154(b) by 0 days.

(21) Appl. No.: 18/826,555

(22) Filed: Sep. 6, 2024

(65) Prior Publication Data

US 2025/0104864 A1 Mar. 27, 2025

Related U.S. Application Data

(60) Provisional application No. 63/539,865, filed on Sep. 22, 2023.

(51) Int. Cl.
*G16H 50/20* (2018.01)
*G06T 7/00* (2017.01)
(Continued)

(52) U.S. Cl.
CPC ........... *G16H 50/20* (2018.01); *G06T 7/0012* (2013.01); *G06V 10/762* (2022.01); *G16H 10/20* (2018.01);
(Continued)

(58) Field of Classification Search
CPC ........ G16H 50/20; G16H 50/30; G16H 50/70; G16H 10/20; G06V 10/762; G06T 7/0012
See application file for complete search history.

(56) References Cited

U.S. PATENT DOCUMENTS 11,417,418 B1 * 8/2022 Jain ........................ H04L 41/147
11,514,339 B2 * 11/2022 Burke .................... G16H 50/70
(Continued)

FOREIGN PATENT DOCUMENTS

WO WO-2007145900 A2 * 12/2007 ............. G06Q 10/10

OTHER PUBLICATIONS

Ping et al., "Breast Cancer Symptom Clusters Derived From Social Media and Research Study Data Using Improved K-Medoid Clustering," IEEE Transactions on Computational Social Systems, vol. 3, No. 2, Jun. 2016; Digital Object Identifier 10.1109/TCSS.2016.2615850. (Year: 2016).*

(Continued)

*Primary Examiner* — Jonathon A. Szumny
(74) *Attorney, Agent, or Firm* — Samuel J. Gee

(57) ABSTRACT

Systems and methods for generating a personal profile and a recommendation based on the generated personal profile. The method includes generating a plurality of clusters, each cluster of the generated plurality of clusters including at least a set of variables for users included in the cluster, the set of variables related to at least one of gender, age, skin tone, acne marks, acne frequency, a lesion score, or a body distribution score, generating, for a new user, a profile, associating the generated profile into a cluster of the plurality of clusters, and generating, by a machine learning (ML) model, a recommendation for the user based on the associated cluster.

20 Claims, 11 Drawing Sheets

(51) Int. Cl.

| | |
|---|---|
| ***G06V 10/762*** | (2022.01) |
| ***G16H 10/20*** | (2018.01) |
| ***G16H 20/10*** | (2018.01) |
| ***G16H 50/30*** | (2018.01) |
| ***G16H 50/70*** | (2018.01) |

(52) U.S. Cl.

CPC ............. *G16H 20/10* (2018.01); *G16H 50/30* (2018.01); *G16H 50/70* (2018.01); *G06T 2207/30201* (2013.01)

(56) References Cited

U.S. PATENT DOCUMENTS

| | | | | |
|---|---|---|---|---|
| 11,823,785 | B2 * | 11/2023 | Neumann | G16H 20/60 |
| 2017/0329917 | A1 * | 11/2017 | McRaith | G16H 20/00 |
| 2020/0143922 | A1 * | 5/2020 | Chekroud | G16H 20/10 |
| 2020/0275886 | A1 * | 9/2020 | Mason | A61B 5/4824 |
| 2021/0118559 | A1 * | 4/2021 | Lefkofsky | G16B 20/00 |
| 2021/0257093 | A1 * | 8/2021 | Griffin | G16H 50/20 |
| 2022/0139554 | A1 * | 5/2022 | Pillay | G16H 70/20 705/2 |
| 2022/0172838 | A1 * | 6/2022 | Besanson | G06N 20/10 |
| 2022/0406405 | A1 * | 12/2022 | Durham | G16H 20/00 |
| 2023/0352142 | A1 * | 11/2023 | Rosenberg | A63B 21/00178 |
| 2024/0071627 | A1 * | 2/2024 | Behal | G16H 50/70 |
| 2024/0079137 | A1 * | 3/2024 | Nathan | G16H 50/20 |
| 2024/0274291 | A1 * | 8/2024 | Basu | G16H 50/70 |

OTHER PUBLICATIONS

Nappi et al., “Menopause: a cardiometabolic transition,” The Lancet Diabetes & Endocrinology; vol. 10, Issue 6, Jun. 2022; https://doi.org/10.1016/S2213-8587(22)00076-6. (Year: 2022).*

Hong Qing Yu, “Extracting Reliable Health Condition and Symptom Information to Support Machine Learning,” 2019 IEEE SmartWorld, Ubiquitous Intelligence & Computing, Advanced & Trusted Computing, Scalable Computing & Communications, [ ]; DOI: 10.1109/SmartWorld-UIC-ATC-SCALCOM-IOP-SCI.2019.00300. (Year: 2019).*

Bonaccorsi et al., “Predicting treatment recommendations in postmenopausal osteoporosis,” Journal of Biomedical Informatics 118 (2021) 103780; https://doi.org/10.1016/j.jbi.2021.103780. (Year: 2021).*

Tian et al., “Screening for chronic conditions with reproductive factors using a machine learning based approach,” Scientific Reports | (2020) 10:2848 | https://doi.org/10.1038/s41598-020-59825-3. (Year: 2020).*

International Search Report/Written Opinion—PCT/IB2024/058717 Dated Jan. 3, 2025.

Genius Katalin: “Douglas launches new AI tool for skin analysis,” Jul. 13, 2022, pp. 1-2 (XP093223757).

Tseng Johnny: “Transform the Beauty Industry through AI + AR PerfectCorp’s innovative vision into the digital era,” Jul. 6, 2022, pp. 1-43. (XP093223763).

Perfect Corp | Beauty Tech AI & AR: “AI Skin Analysis | How It Works | Skin Analyzer, Diagnostic, Smoothing Emulations & More,” Sep. 13, 2022—Retrieved from the Internet: https://www.youtube.com/watch?v=6WrSqY6UmPE (XP093223768).

* cited by examiner

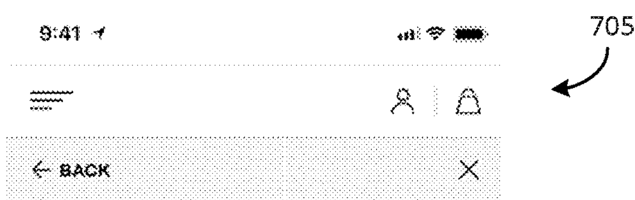

ALMOST DONE!

We're creating personalized results based on your answers. Just enter your first name and email address, and we'll send it your way.

First name*

Hint text

Email address*

Hint text

☐ I agree to the collection and use of my Sensitive Personal Information (SPI) such as ethnicity or any health-related information. I understand that the information will be used in accordance with the Privacy Policy.*

☐ I would like to receive news and offers from Versalie*.

The information you submit will be governed by our Privacy Policy and you agree to the Financial Incentive Notice.

FIG. 7E

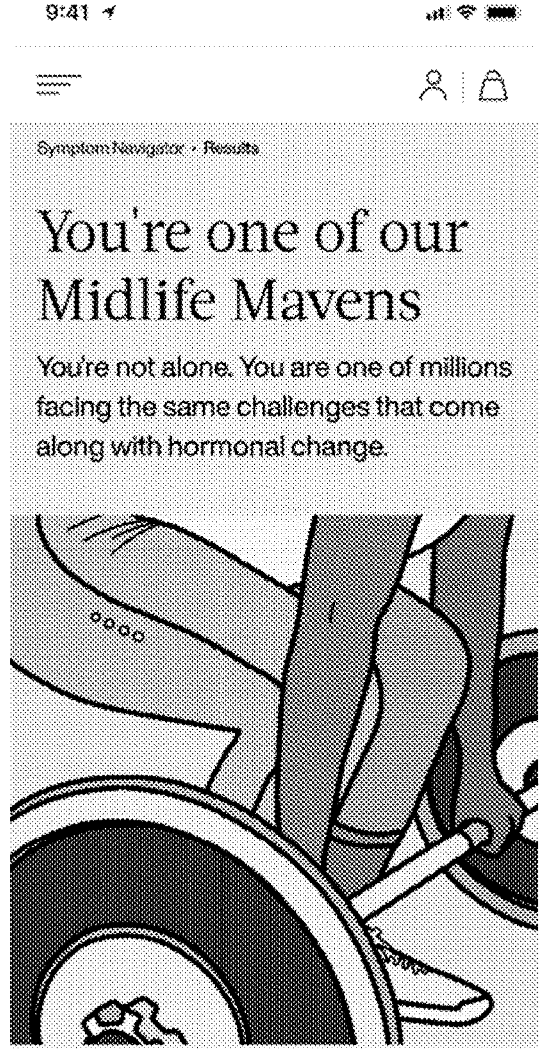

FIG. 7F

707

PERSONAL PROFILE GENERATOR AND RECOMMENDATION ENGINE

CROSS-REFERENCE TO RELATED APPLICATIONS

This application claims the benefit of U.S. Provisional Application No. 63/539,865, filed Sep. 22, 2023, the contents of which is incorporated herein by reference in its entirety.

BACKGROUND

Consumers oftentimes perform individual research on a particular condition or phase of life, such as menopause, they believe they may be experiencing or soon experiencing and, based on their research, select a healthcare product, or products, that may alleviate symptoms. Oftentimes, this leads to self-diagnosis by the consumer and the particular healthcare product is selected based on an advertisement, word of mouth, or selection in store or online. However, the self-diagnosis may not be correct and/or may not take into account the root cause of a particular symptom or symptoms, and the selected product may not be the most effective product for the root cause of the symptom. This may be due to the consumer identifying incorrect or incomplete information, leading to an incorrect self-diagnosis, and/or the selected products failing to address the symptoms felt by the consumer.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one example, a computer-implemented method is provided. The method includes generating a plurality of clusters; generating, for a new user, a profile; associating the generated profile into a cluster of the plurality of clusters; and generating, by a machine learning (ML) model, a recommendation for the user based on the associated cluster.

In another example, an apparatus is provided. The apparatus includes a user interface (UI); a memory; and a processor coupled to the memory configured to: control the UI to present a questionnaire; receive, via the UI, a response to the questionnaire; generate a profile associated with the user based on the received responses to the questionnaire and the captured facial scan; associate the generated profile into a cluster of a plurality of clusters; and execute a machine learning (ML) model to generate a recommendation for the user based on the associated cluster.

In another example, a computer-readable storage media is provided. The computer-readable storage media stores instructions that, when executed by a processor, cause the processor to generate a plurality of clusters, each cluster of the generated plurality of clusters including at least a stage of menopause and symptoms experienced related to menopause; generate, for a new user, a profile, the generated profile including at least an identified user stage of menopause and user symptoms experienced related to menopause; associate the generated profile into a cluster of the plurality of clusters; and generating, by a machine learning (ML) model, a recommendation for the user based on the associated cluster.

Other technical features may be readily apparent to one skilled in the art from the following figures, descriptions, and claims.

BRIEF DESCRIPTION OF THE DRAWINGS

The present description will be better understood from the following detailed description read in light of the accompanying drawings, wherein:

FIGS. 7A-7G illustrate example UIs of a flow including creating a profile, receiving data, and generating a recommendation.

Corresponding reference characters indicate corresponding parts throughout the drawings. In FIGS. 1 to 8, the systems are illustrated as schematic drawings. The drawings may not be to scale.

DETAILED DESCRIPTION

Figure 1:
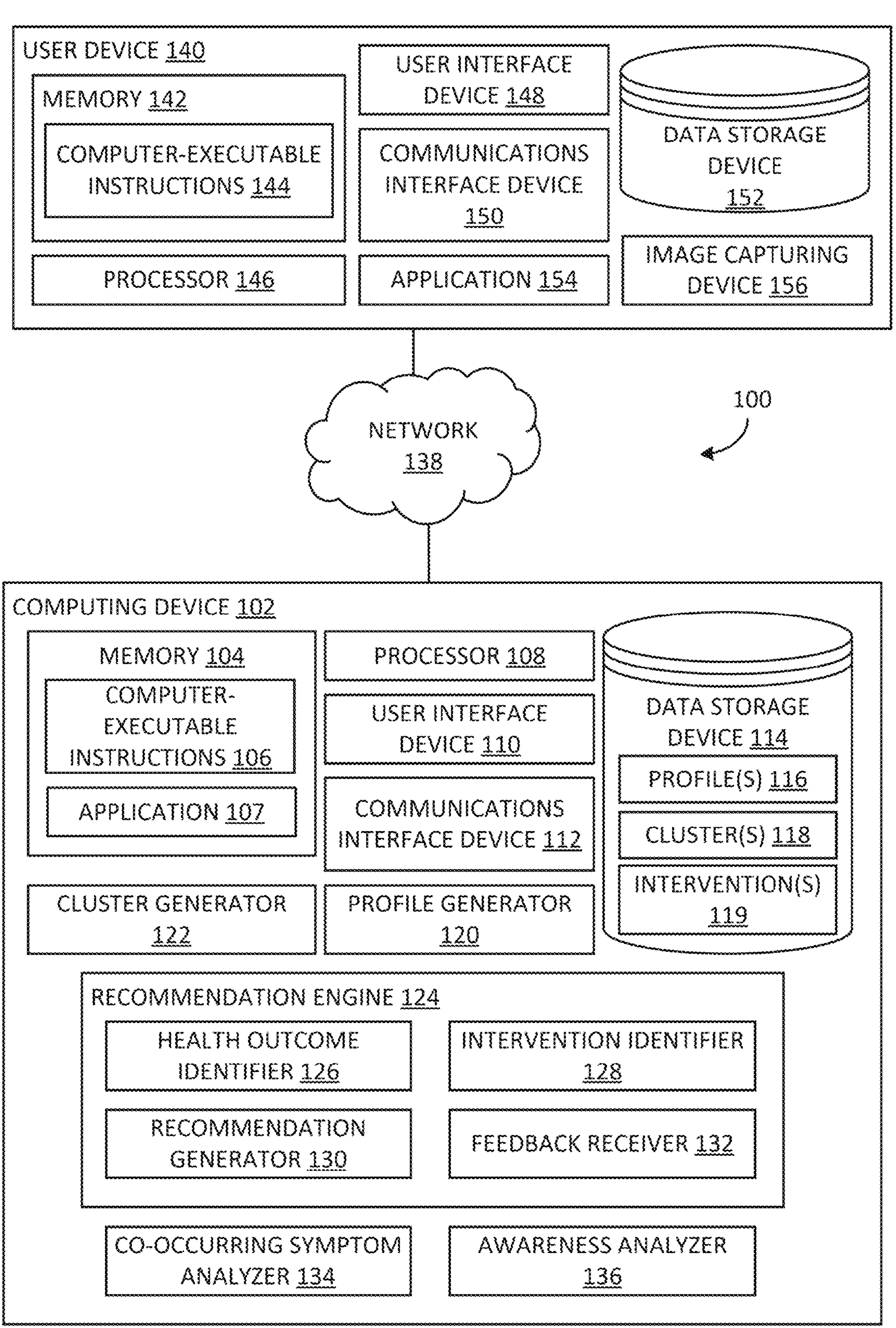
FIG. 1 illustrates an example system for generating a personal profile and a recommendation based on the generated personal profile.

The various implementations and examples will be described in detail with reference to the accompanying drawings. Wherever possible, the same reference numbers will be used throughout the drawings to refer to the same or like parts. References made throughout this disclosure relating to specific examples and implementations are provided solely for illustrative purposes but, unless indicated to the contrary, are not meant to limit all examples.

As described herein, identification of a particular condition or phase of life, such as menopause, is traditionally performed by a consumer via self-diagnosis. This further leads to selection of a healthcare product, or products, that may alleviate symptoms of self-diagnosed menopause. This also results in the selection of a particular healthcare product based on an advertisement, word of mouth, or selection in store or online without scientific data backing up the selection, as the self-diagnosis may not be correct and/or may not take into account the root cause of a particular symptom or symptoms. Current solutions fail to adequately take into account the particular condition, co-occurrences in symptoms due to ethnicity, income, or awareness, or provide resources to help educate women undergoing menopause and assist them in the selection of products or services to treat their particular symptoms based on their profile.

Accordingly, aspects of the present disclosure provide systems and methods for generating a personal profile for a consumer, identifying one or more underlying causes of one or more conditions, and generating, using artificial intelligence (AI), holistic product and/or lifestyle recommendations to address the one or more conditions. In some examples, the recommendations are updated over time to incorporate feedback regarding the implementation of a recommendation, a change in the condition or the profile of the consumer, and so forth. The systems and methods described herein operate in an unconventional manner by collecting data from various sources and in various formats for a new profile, converting the collected data into a standardized format, generating clusters of similar profiles and associating the new profile with a particular cluster, determining an expected health outcome for the profiles in the cluster and identifying an associated intervention, and generating a recommendation that, when applied, implements the intervention to address the expected health outcome. In some examples, the present disclosure further identifies unexpected co-occurrences between different ethnicities, incomes, and awareness of menopause to generate the clusters and recommendations. The present disclosure therefore provides numerous technical effects, including an improved data structure that stores the converted data originally collected from multiple sources that facilitates improved retrieval of the information, an improved recommendation engine that implements a trained machine learning model to optimizes the content delivered, i.e., the generated recommendation, to a consumer based on specific historical user characteristics, taking into account changes in the consumer's profile over time.

For example, the present disclosure provides a profile generator that generates a profile for a consumer. The profile includes variables related to consumer data including, but not limited to, age, ethnicity, income, geographical location, awareness of menopause, various menopause-related symptoms, and so forth. A cluster generator generates a cluster of similar profiles. Similar profiles are profiles that have a determined similarity to be above a similarity threshold based on the values of the variables. A recommendation engine generates a health outcome for a particular cluster, identifies an intervention for the health outcome, and generates a recommendation including the intervention. The recommendation is provided to the consumer. In some examples, the recommendation engine receives feedback regarding the provided recommendation and is updated, based on the received feedback, to improve further recommendations. In some examples, the cluster into which a particular profile is associated changes over time. For example, as a consumer's age, symptoms, geographical location, and awareness changes, such as based on the implementation of a recommended intervention, the profile is more closely associated with a different cluster. The recommendation engine then generates an updated recommendation based on the new cluster.

Various examples described here provide a proactive application, or kit, to deliver physical interventions that will change health outcomes. In some examples, the application is an aspect of one or more bundled products that includes the application, content, and a gamified journey point system.

In some examples, the cluster a particular profile is associated with changes over time. For example, as a consumer's age changes, recommendations are implemented that change the profile of the consumer, and so forth, the profile transitions from one cluster to another over time. This is referred to as a personal trajectory. Accordingly, aspects of the present disclosure enable a journey for a consumer to identify causes of menopause-related symptoms, such as such as age, geographical location, and co-occurrence of symptoms, and the reasoning behind those causes, as well as what traits and characteristics a consumer may be prone to, and provides recommendations that include interventions to understand how to address and mitigate negative traits and characteristics and enhance positive traits and characteristics.

As described herein, various examples of the present application provide a technical solution to the inherently technical problem of identifying similarities between digital profiles and associating a newly generated profile with a group of existing profiles based at least in part on digital image analysis, and further detecting changes to a profile over time in order to maintain association of the profile with the closest group of existing profiles. This solution provides at least two technical advantages, including reducing the consumption of computing resources over existing solutions that begin a new categorization process of a user each time an update is made to a user's profile, and generating and implementing an improved set of indexes to facilitate the retrieval of the profile and/or cluster information of a user for the generation of a user recommendation.

FIG. 1 an example system for generating a personal profile and a recommendation based on the generated personal profile. The system 100 illustrated in FIG. 1 is provided for illustration only. Other examples of the system 100 can be used without departing from the scope of the present disclosure. In some examples, the system 100 generates a personal profile and recommendation based on a user experiencing a particular phase of life, such as menopause.

The system 100 includes a computing device 102, a network 138, and a user device 140. The computing device 102 represents any device executing computer-executable instructions 106 (e.g., as application programs, operating system functionality, or both) to implement the operations and functionality associated with the computing device 102. The computing device 102 in some examples includes a mobile computing device or any other portable device. A mobile computing device includes, for example but without limitation, a mobile telephone, laptop, tablet, computing pad, netbook, gaming device, and/or portable media player. The computing device 102 can also include less-portable devices such as servers, desktop personal computers, kiosks, or tabletop devices. Additionally, the computing device 102 can represent a group of processing units or other computing devices.

In some examples, the computing device 102 includes at least one processor 108, a memory 104 that includes the computer-executable instructions 106, and a user interface device 110. The processor 108 includes any quantity of processing units and is programmed to execute the computer-executable instructions 106. The computer-executable instructions 106 are performed by the processor 108, performed by multiple processors within the computing device 102, or performed by a processor external to the computing device 102. In some examples, the processor 108 is programmed to execute computer-executable instructions 106 such as those illustrated in the figures described herein, such as FIG. 8. In various examples, the processor 108 is configured to execute one or more of a profile generator 120, cluster generator 122, recommendation engine 124, co-occurring symptom analyzer 134, and awareness analyzer 136.

The memory 104 includes any quantity of media associated with or accessible by the computing device 102. In some examples, the memory 104 is internal to the computing device 102. In other examples, the memory 104 is external to the computing device 102 or both internal and external to the computing device 102. For example, the memory 104 can include both a memory component internal to the computing device 102 and a memory component external to the computing device 102. The memory 104 stores data, such as one or more applications 107. The applications 107, when executed by the processor 108, operate to perform various functions on the computing device 102. The applications 107 can communicate with counterpart applications or services, such as web services accessible via the network 138. In an example, the applications 107 represent server-side services of an application executing in a cloud, such as a cloud server. In some examples, the application 107 is an application for assisting a user experiencing a particular phase of life, such as menopause, and generating a recommendation for one or more products and/or lifestyle changes to address symptoms believed to be caused by the particular phase of life.

The user interface device 110 includes a graphics card for displaying data to a user and receiving data from the user. The user interface device 110 can also include computer-executable instructions, for example a driver, for operating the graphics card. Further, the user interface device 110 can include a display, for example a touch screen display or natural user interface, and/or computer-executable instructions, for example a driver, for operating the display. The user interface device 110 can also include one or more of the following to provide data to the user or receive data from the user: speakers, a sound card, a camera, a microphone, a vibration motor, one or more accelerometers, a BLUETOOTH® communication module, global positioning system (GPS) hardware, and a photoreceptive light sensor. In a non-limiting example, the user inputs commands or manipulates data by moving the computing device 102 in one or more ways.

The computing device 102 further includes a communications interface device 112. The communications interface device 112 includes a network interface card and/or computer-executable instructions, such as a driver, for operating the network interface card. Communication between the computing device 102 and other devices, such as but not limited to the user device 140, can occur using any protocol or mechanism over any wired or wireless connection.

The computing device 102 further includes a data storage device 114 for storing data, such as, but not limited to one or more profiles 116, clusters 118, and/or interventions 119. The data 114 can be data received from the user device 140 and/or data received, retrieved, or obtained by one or more of the profile generator 120, cluster generator 122, recommendation engine 124, co-occurring symptom analyzer 134, and awareness analyzer 136. The profile(s) 116 includes at least one profile for a particular consumer, including data values regarding variables for the consumer. In some examples, the profile, data values, and variables depend on the type of application, or applications, 107 executed on the computing device 102. For example, where the application 107 is a menopause-related application, the variables may include, but are not limited to, age, number of symptoms, types of symptoms, severity of symptoms, ethnicity, income, geographical location, awareness of menopause and so forth. Each profile 116 corresponds to a different consumer and is generated by the profile generator 120. The cluster(s) 118 includes at least one cluster that includes a selected set of profiles 116 that have a similarity score above a similarity threshold. Each cluster 118 is generated by the cluster generator 122. The intervention(s) 119 include interventions, as described below, approved for treatment of various health outcomes, such as products, lifestyle adjustments, or a combination of these.

In some examples, such as where the system 100 is a system for generating menopausal profiles and recommendations, the data storage device 114 stores an index that associates menopausal symptoms with ranking values for symptoms and resources to address those symptoms. The symptoms may be ranked according to various methodologies, including most frequent symptoms observed during menopause, most frequent symptoms observed during a particular stage of menopause, a likelihood that treatment or relief will be sought by a consumer for the symptoms, and so forth. In various examples, the resources include, but are not limited to, articles, videos, products, licensed medical professionals, and so forth. In other examples, the index includes data associated with the co-occurrence of different menopausal symptoms. For example, index may include data indicating common co-occurring symptoms for various symptoms, such as fatigue, insomnia, anxiety, depression, hot flashes, night sweats, joint pain, arthritis, headaches, migraines, loss of libido, cognitive changes such as memory issues or loss of mental sharpness, irregular heartbeat, weight gain, or changes in body odor, based on ethnicity. The data included in the index may be collected from various sources, including Examples 1 and 2 below.

Example 1

A first study, conducted with an objective of studying and identifying how menopause symptoms vary across different demographic groups, particularly ethnicity and income levels, focused on a range of symptoms including vasomotor, sleep, and cognitive symptoms along with mental and sexual health. The first study was conducted among 4,578 female participants aged 40-65 years (Mean=50.2, SD=7.6) in the United States. Participants completed an online survey over a three-week period, with a mean completion time of 25 minutes per person. To ensure validity of responses, participants were excluded if anyone in their close network works in the healthcare ecosystem. In total, the first study enrolled Caucasian (n=2,936), African American (n=665), Asian (n=147), Native American (n=41), Hispanic (n=665) women and other ethnicities (n=124). The study included 118 questions on health attitudes, treatment history, knowledge of HRT, and proposed solutions. To identify symptom co-occurrences, Phi correlations were conducted for paired symptoms at the individual level for each ethnic group. One-way ANOVA was used to evaluate the ethnic group variations in the number of co-occurring symptoms with group means adjusted by sample sizes. The role of income in symptom co-occurrences was assessed by recording significant pairs for each income group and conducting chi-square tests across income levels.

Example 1—Results

Correlations across the symptom occurrences showed that women experience multiple symptoms simultaneously: rs=0.3~0.6, ps<0.05~0.005. One-way ANOVA revealed a significant effect of ethnicity on the number of significant co-occurring symptoms (F=13.0, p<0.001). Pairwise comparisons showed that the Native American group reported significantly more co-occurring symptoms than all other ethnic groups: ps<0.05. The results are shown in Table 1 below.

TABLE 1

| Number of co-occurring symptoms by ethnicity | | | | | |
|---|---|---|---|---|---|
| Symptom | African American | Asian | Caucasian | Hispanic | Native American |
| Hot flashes | 3 | 4 | 9 | 3 | 25 |
| Night sweats | 6 | 1 | 7 | 6 | 18 |
| Changes in body odor | 5 | 1 | 2 | 6 | 30 |
| Headaches | 3 | 11 | 16 | 13 | 17 |
| Migraine | 2 | 12 | 5 | 1 | 37 |
| Loss of Libido | 8 | 7 | 12 | 5 | 28 |
| Loss of Mental Sharpness | 21 | 12 | 22 | 25 | 35 |
| Memory issues | 16 | 14 | 24 | 20 | 22 |
| Irregular Heartbeat | 1 | 8 | 0 | 1 | 20 |
| Weight gain | 2 | 11 | 9 | 9 | 21 |
| Fatigue | 18 | 19 | 22 | 28 | 31 |
| Insomnia | 17 | 20 | 14 | 13 | 35 |
| Depression | 16 | 14 | 22 | 13 | 25 |
| Anxiety | 12 | 19 | 20 | 15 | 30 |

Unexpectedly, different ethnic groups of women experience common and unique menopausal symptoms. For instance, hot flashes were accompanied by night sweats and mood swings across all ethnicities. In addition, African American women experienced insomnia, Caucasians had irritability, loss of libido, insomnia, and cognitive issues, Asian women showed vaginal dryness, Hispanics noted changes in body odor, and Native Americans had up to 25 symptoms including headaches. The chi-square test revealed a significant effect of income in the number of co-occurring symptoms: $X2(3,4)=59.2$, $p<0.001$. Tukey's HSD pairwise analyses showed a significant sequential decrease in co-occurring symptoms with increasing income levels: under \$35 k, \$35 k-\$75 k, \$75 k-\$150 k, and above \$150 k ($ps<0.05\sim0.001$).

Accordingly, the findings align with the SWAN study findings that women experience various symptoms related to menopause. The findings also illustrate that ethnicity significantly influences symptom experiences, informing clinical practices. The findings can aid in menopause diagnosis through symptom screening and guide healthcare providers in tailored questioning. Additionally, the research suggests the importance of utilizing genetic testing to better understand ethnic patterns and genetic variability, as well as facilitating targeted treatments for diverse groups of women.

Example 2

A second study, conducted with a goal of providing more insights on women's perceptions and experiences with MHT, focused on potential age-related variations as the topic of MHT remains controversial and polarizing among patients. Previous research conducted by the Women's Health Initiative has demonstrated a connection between MHT and an increased risk of coronary heart disease and breast cancer. Consequently, MHT use and new prescriptions significantly decreased. The second study was conducted among 4,578 female participants aged 40-65 years (Mean=50.2, SD=7.6) in the United States. Participants completed the online survey over a three-week period, with an average completion time of 25 minutes per participant. To ensure validity of responses, participants were excluded if anyone in their close network works in the healthcare ecosystem. In total, the second study enrolled Caucasian (n=2,936), African American (n=665), Asian (n=147), Native American (n=41), Hispanic (n=665) women and other ethnicities (n=124). The study included 118 questions on health attitudes, treatment history, knowledge of MHT, and proposed solutions. The current study evaluated differences in women's self reported knowledge and attitudes towards MHT by age group.

To identify the role of MHT knowledge on women's attitudes toward MHT, Spearman correlations were conducted for paired symptoms at the individual level within each ethnic group. To examine the age variations, women were categorized into 4 age groups: 40-45 years, 45-50 years, 50-60 years, and 60-65 years. Kruskal-Wallis tests were utilized to compare differences in attitudes towards MHT across age groups. Post hoc Dunn's tests (FDR corrected) were then conducted for pairwise comparisons to examine specific age group distinctions in each attitude towards MHT.

Example 2—Results

Correlation results showed a significant association between greater knowledge of MHT and emotional responses towards MHT ($ps<0.001$). Higher levels of MHT knowledge were related to more positive feelings and fewer negative feelings. Better MHT knowledge being significantly associated with more positive attitudes towards MHT was reflected by survey responses including feelings of optimism regarding the helpfulness of MHT and relief at starting MHT ($rs=0.2\sim0.25$, $ps<0.001$). Simultaneously, increased knowledge of MHT was significantly correlated with reduced negative attitudes, as evidenced by survey responses reflecting feelings of inadequacy in managing menopause independently, uncertainty regarding MHT, and reluctance to discuss MHT with family and friends ($rs=-0.2\sim-0.24$, $ps<0.001$). Regarding the age-related variations, the Kruskal-Wallis test results showed significant differences among groups in certain attitudes, with older adults 55 to 65 having stronger positive attitudes towards MHT compared to younger adults 40 to 50 ($Hs=15.7\sim256.0$, $ps<0.01\sim0.001$). Among the top three survey attitude responses exhibiting substantial age-related variances, post hoc Dunn's pairwise analyses identified significant age differences across all four age groups, with the exception of the following two pairs: 40-45 years vs. 45-50 years, and 55-60 years vs. 60-65 years. These attitudes included feelings of inadequacy in managing menopause independently, reluctance to discuss MHT with family and friends, and uncertainty regarding MHT. Older women are also more willing to consider MHT and feel a sense of responsibility to share about MHT with more women.

Accordingly, the second study indicates that older women 55 to 65 have a greater understanding of MHT, exhibit more positive attitudes towards MHT, and are more receptive to utilizing MHT compared to younger women 40 to 50. These findings underscore a key opportunity to educate the next generation of women who are undergoing the menopause transition. These findings offer valuable insights for clinicians, enabling them to better comprehend the potential perceptions of MHT among patients across various age groups, and facilitating proactive discussions about MHT.

The data storage device 114 can include one or more different types of data storage devices, such as, for example, one or more rotating disks drives, one or more solid state drives (SSDs), and/or any other type of data storage device. The data storage device 114 in some non-limiting examples includes a redundant array of independent disks (RAID) array. In other examples, the data storage device 114 includes a database. The data storage device 114, in this example, is included within the computing device 102, attached to the computing device 102, plugged into the computing device 102, or otherwise associated with the computing device 102. In other examples, the data storage device 114 includes a remote data storage accessed by the computing device 102 via the network 138, such as a remote data storage device, a data storage in a remote data center, or a cloud storage.

The computing device 102 further includes a profile generator 120. In some examples, the profile generator 120 is an example of a specialized processor, or processing unit, implemented on the processor 108. The profile generator 120 generates a profile for a consumer based on data received from the consumer, such as data input on the external device 140 and transmitted to the computing device 102. For example, the profile generator 120 receives raw data from the consumer in various data formats, i.e., textual formats, numerical formats, etc., and converts, or transforms, the received data into a standardized data format. The standardized data is stored in the data storage device 114 as the profile 116.

The computing device 102 further includes a cluster generator 122. In some examples, the cluster generator 122 is an example of a specialized processor, or processing unit, implemented on the processor 108. The cluster generator 122 generates a cluster that includes at least two profiles. To generate a cluster, the cluster generator 122 determines the similarity between a particular profile and each additional profile. In some examples, a profile is added to a particular cluster when the profile has a similarity threshold with the other profiles that are included in the cluster that reaches or exceeds a similarity threshold. The similarity threshold may be a threshold percentage of data values of the profiles that are the same or similar, a threshold number of the data values that are the same, one or more particular values that are the same, or any other suitable threshold for determining similarity. In some examples, the cluster generator 122 generates a persona, or phenotype, associated with each generated cluster. The generated persona includes an artificial profile that represents the data values of the profiles in the cluster.

The computing device 102 further includes a recommendation engine 124. In some examples, the recommendation engine 124 is an example of a specialized processor, or processing unit, implemented on the processor 108. The recommendation engine 124 generates one or more recommendations based on the consumer profile and/or the cluster to which the consumer profile belongs. The recommendation engine 124 generates a recommendation based on the type of system 100 to which the recommendation engine 124 belongs. For example, where the system 100 is a system for generating menopausal profiles and recommendations, the recommendation engine 124 generates a recommendation for addressing menopausal symptoms.

The recommendation engine 124 includes a health outcome identifier 126, an intervention identifier 128, a recommendation generator 130, and a feedback receiver 132. The health outcome identifier 126 identifies a health outcome associated with a particular cluster. In some examples, the health outcomes include a condition, such as menopause, and a stage of menopause, such as perimenopause, menopause, or post-menopause. In some examples, the identified health outcomes are stored as a value of the cluster 118 in the data storage device 114.

The intervention identifier 128 identifies a particular intervention that, when applied, are anticipated to alleviate or mitigate the identified health outcome based on research data, clinical data, and so forth. Various examples of an intervention include a product, a combination of two or more products, a lifestyle adjustment, a combination of two or more lifestyle adjustments, a combination of at least one product and at least one lifestyle adjustment, and so forth. In some examples, the interventions are stored in the data storage device 114 as interventions 119 crossed reference with health outcomes. In some examples, the interventions 119 are ranked according to an anticipated outcome. For example, an intervention 119 having a greater likelihood of a positive outcome is ranked higher than an intervention 119 having a lower likelihood of a positive outcome. In another example, an intervention 119 having a greater potential effect is ranked higher than an intervention having a lower potential effect.

The recommendation generator 130 generates a recommendation for a consumer associated with a particular profile. In examples where the intervention identifier 128 identifies one potential intervention, the generated recommendation includes the intervention 119 identified by the intervention identifier 128 and instructions for implementation of the identified intervention 119. In examples where multiple potential interventions are identified, the recommendation generator 130 generates a recommendation that includes the highest ranked intervention 119 or a set of the highest ranked interventions. In some examples, the recommendation generator 130 selects an intervention 119 or interventions 119 based on weighing a likelihood of engagement and compliance with the intervention, stage of menopause, and a holistic view of overall health based on the symptoms and severity of symptoms.

In some examples, the generated recommendation further includes educational resources associated with the particular stage of life. For example, the educational resources include content, such as articles, videos, podcasts, and so forth, that include educational material associated with a particular sub-segment of the stage of life, products that assist with the treatment of symptoms of the stage of life, lifestyle adjustments that may assist with the treatment of symptoms of the stage of life, and so forth.

In some examples, an intervention includes a particular product and/or a lifestyle adjustment. The generated recommendation includes instructions for implementing the intervention, such as a quantity of the product to be applied a set number of times per day or per week. For example, the generated recommendation includes the use of two products, such as a product to treat each of headaches and hot flashes, instructions to use the two products according to a particular protocol, and educational resources associated with the particular stage of menopause and the particular symptoms of the user. It should be understood that this example of a recommendation is presented for illustration only and should not be construed as limiting. Various examples of a generated recommendation are possible without departing from the scope of the present disclosure. In some examples, recommendations for a particular product or products includes a link to a website where the recommended product is available for purchase by the consumer.

The feedback receiver 132 receives feedback regarding a generated recommendation. In some examples, the feedback is received via the user interface device 110. In other examples, the feedback is received via the communications interface device 112 from an external device, such as a user device 140, of the consumer that implements the generated recommendation. The received feedback includes one or more indications regarding the success, failure, and/or viability of the generated recommendation. In an example where the generated recommendation includes the one or more products and associated instructions to treat symptoms of menopause, the feedback may be that the generated recommendation resulted in positive results, e.g., reduced hot flashes, night sweats, or joint pain, negative results, e.g., no change in symptoms, or non-viability, such as the generated recommendation was difficult to implement due to complex instructions, too much time was required to correctly follow the instructions, and so forth. In some examples, feedback is received through the completion of a user survey, where a consumer provides scaled ratings for various elements of the recommendation, such as a scale of one to ten, one to five, and so forth. In other examples, feedback is received based on user data that maps whether the recommended product was purchased through the provided link, whether the recommended product was purchased at a later time, whether the recommended product was purchased multiple times, and so forth. In these examples, the feedback receiver 132 analyzes the received feedback and provides the analyzed feedback to the recommendation generator 130.

The recommendation generator 130 is updated based on the received feedback. For example, positive feedback is used to reinforce the generated recommendation, while negative feedback or feedback that a recommendation is non-viable is implemented so that a future recommendation for the consumer and/or other profiles in the same cluster as the consumer includes a different product, different combination of products, different instructions for implementing the product or products, and so forth.

In some examples, the received feedback is further used by the profile generator 120 to update the profile. For example, feedback received that indicates reduced symptoms of menopause automatically updates the profile for the consumer to reflect the reduced symptoms. In some examples, based on the updated profile, the cluster generator 122 re-clusters the updated profile based on the updated information. For example, the cluster generator 122 re-clusters the updated profile into a new cluster that includes other profiles with similar symptoms and levels of those symptoms. Based on the updated cluster for the profile, the recommendation generator 130 generates an updated recommendation for the consumer to reflect the updated profile and cluster, including but not limited to a product, a combination of two or more products, a lifestyle adjustment, a combination of two or more lifestyle adjustments, a combination of at least one product and at least one lifestyle adjustment, and so forth, where the products and lifestyle adjustments may be the same or different than the originally recommendation products or lifestyle adjustments, respectively.

In some examples, as described herein, the system 100 is a system for generating a recommendation for addressing menopausal symptoms. For example, the profile generator 120 generates a profile 116 for a consumer that includes information related to the consumer's age, types of menopausal symptoms, number of menopausal symptoms, severity of menopausal symptoms, and so forth. The cluster generator 122 places the consumer in a cluster 118 according to a similarity between the profile of the consumer and other profiles in the cluster. The recommendation engine 124 generates a recommendation for the consumer based on the cluster 118.

In this example, the health outcome identifier 126 identifies the health outcome as menopause, such as based on the age and symptom information provided by the consumer. The intervention identifier 128 identifies the highest ranked symptoms identified for the consumer, or the for the persona in the cluster 118, according to the ranking stored in the data storage device 114. For example, as described herein, the symptoms may be ranked most frequent symptoms observed during menopause, most frequent symptoms observed during a particular stage of menopause, a likelihood that treatment or relief will be sought by a consumer for the symptoms, and so forth. In one example, the symptoms are ranked according to a likelihood that treatment or relief will be sought by a consumer for the symptoms, and the intervention identifier 128 identifies a resource associated with each of the top symptoms identified for the persona or, more specifically, by the consumer. For example, the intervention identifier 128 may identify the top symptom, top three symptoms, top five symptoms, and so forth, and identify a resource associated with each identified symptom. As described herein, the identified resources may include one or more of an article or video that provides education and/or suggested treatment for a particular symptom, a product that can be used to reduce or alleviate a symptom, a list of medical professionals available for a medical visit via an in-person appointment or telehealth appointment, and so forth.

The recommendation generator 130 generates a recommendation that includes the identified resources associated with the top identified symptoms. The generated recommendation includes the identified resource for each of the top identified symptoms for the consumer. The recommendation is presented on the user interface device 110 and/or transmitted to the user device 140, where it is presented on the user interface device 148. The feedback receiver 132 receives feedback regarding the generated recommendations, which is used by the recommendation generator 130 for updating.

The user device 140 is another example of a computing device, separate from and external of the computing device 102. In some examples, the user device 140 includes a mobile computing device or any other portable device. A mobile computing device includes, for example but without limitation, a mobile telephone, laptop, tablet, computing pad, netbook, gaming device, and/or portable media player. The user device 140 can also include less-portable devices such as servers, desktop personal computers, kiosks, or tabletop devices. Additionally, the user device 140 can represent a group of processing units or other computing devices.

In some examples, the user device 140 includes at least one processor 146, a memory 142 that includes the computer-executable instructions 144, and a user interface device 148. The processor 146 includes any quantity of processing units and is programmed to execute the computer-executable instructions 144. The computer-executable instructions 144 are performed by the processor 146, performed by multiple processors 146 within the user device 140, or performed by a processor 146 external to the user device 140. In some examples, the processor 146 is programmed to execute computer-executable instructions 144 such as those illustrated in the figures described herein, such as FIG. 8. In various examples, the processor 146 is configured to execute an application 154, which is a client-side version of the application 107.

The memory 142 includes any quantity of media associated with or accessible by the user device 140. In some examples, the memory 142 is internal to the user device 140. In other examples, the memory 142 is external to the user device 140 or both internal and external to the user device 140. For example, the memory 142 can include both a memory component internal to the user device 140 and a memory component external to the user device 140. The memory 142 stores data, such as one or more applications 154. The applications 154, when executed by the processor 146, operate to perform various functions on the user device 140. The applications can communicate with counterpart applications or services, such as web services accessible via the network 138. In an example, the applications represent downloaded client-side applications that correspond to server-side services executing in a cloud, such as a cloud server.

The user interface device 148 includes a graphics card for displaying data to a user and receiving data from the user. The user interface device 148 can also include computer-executable instructions, for example a driver, for operating the graphics card. Further, the user interface device 148 can include a display, for example a touch screen display or natural user interface, and/or computer-executable instructions, for example a driver, for operating the display. The user interface device 148 can also include one or more of the following to provide data to the user or receive data from the user: speakers, a sound card, a camera, a microphone, a vibration motor, one or more accelerometers, a BLUETOOTH® communication module, global positioning system (GPS) hardware, and a photoreceptive light sensor. In a non-limiting example, the user inputs commands or manipulates data by moving the user device 140 in one or more ways.

In some examples, the user interface device 148 is configured to launch and display a visualization of the application 154, such as illustrated in FIGS. 7A-7G. For example, the processor 146 can execute the computer-executable instructions 144 stored in the memory 142 to execute the application 154 and the visualization of the application 154, illustrated in FIGS. 7A-7G, is presented via the user interface device 148.

The user device 140 further includes a communications interface device 150. The communications interface device 150 includes a network interface card and/or computer-executable instructions, such as a driver, for operating the network interface card. Communication between the user device 140 and other devices, such as but not limited to the computing device 102, can occur using any protocol or mechanism over any wired or wireless connection.

The user device 140 further includes a data storage device 152 for storing data, such as, but not limited to user provided data associated with a profile 116 of a consumer who is the user of the user device 140. The data can be data received via the user interface device 148 and/or data received, retrieved, or obtained from the computing device 102.

The data storage device 152 can include one or more different types of data storage devices, such as, for example, one or more rotating disks drives, one or more solid state drives (SSDs), and/or any other type of data storage device. The data storage device 152 in some non-limiting examples includes a redundant array of independent disks (RAID) array. In other examples, the data storage device 152 includes a database. The data storage device 152, in this example, is included within the user device 140, attached to the user device 140, plugged into the user device 140, or otherwise associated with the user device 140. In other examples, the data storage device 152 includes a remote data storage accessed by the user device 140 via the network 138, such as a remote data storage device, a data storage in a remote data center, or a cloud storage.

The user device 140 further includes an image capturing device 156. In some examples, the image capturing device 156 is a camera operable to capture still images and/or video of a consumer's skin. In some examples, the captured images and/or video is used by the recommendation engine 124 to enhance the generated recommendation, as described herein. For example, the captured images and/or video is included in the profile 116 of the user stored in the data storage device 114 and used to provide objective detail regarding the consumer's skin, in comparison to subjective detail that is provided by the user, for example in response to a questionnaire.

Figure 2:
FIG. 2 illustrates an example system for generating a plurality of personas.
Figure 2:
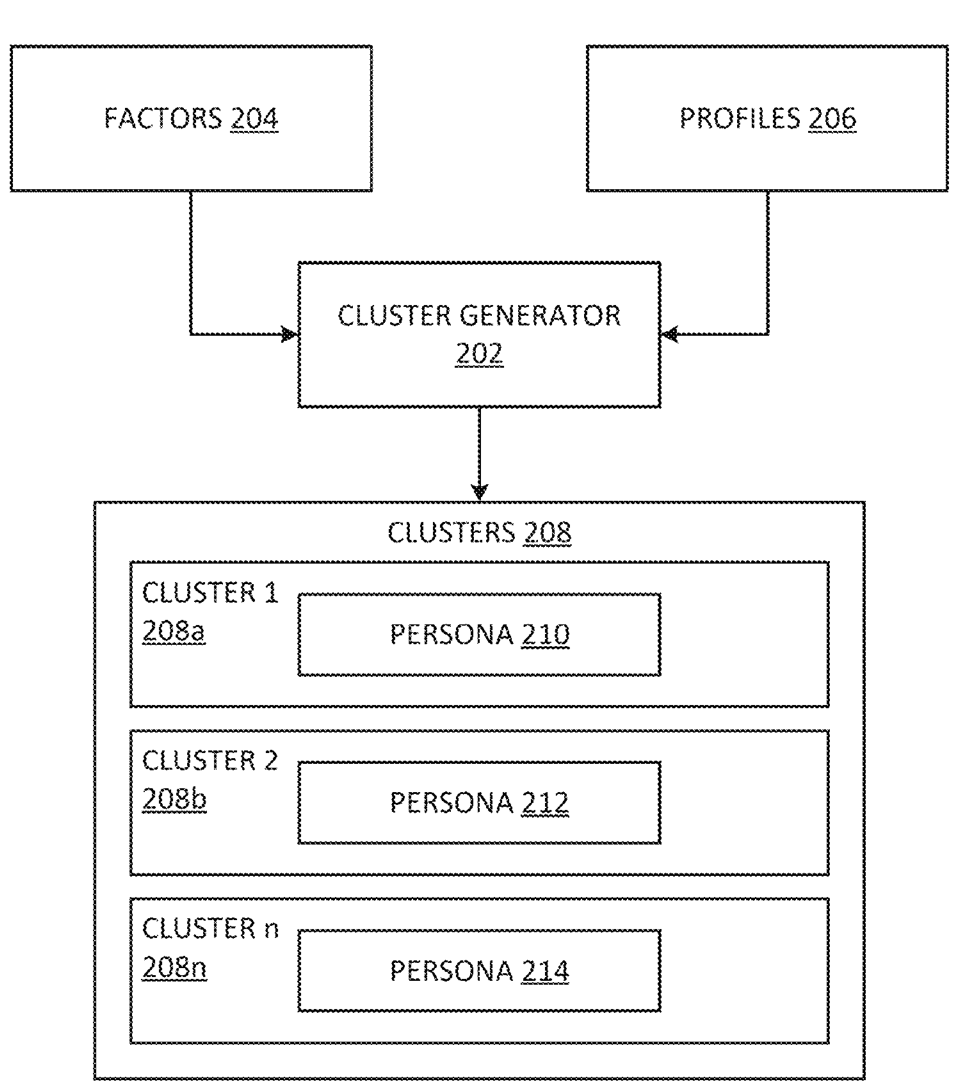

FIG. 2 illustrates an example system for generating a plurality of personas. The example system illustrated in FIG. 2 is for illustration only and should not be construed as limiting. Various examples of the system 200 may be implemented without departing from the scope of the present disclosure. In various examples, the system 200 is implemented by one or more elements of the system 100, such as the cluster generator 122.

The system 200 includes a cluster generator 202. In some examples, the cluster generator 202 is an example of the cluster generator 122 illustrated in FIG. 1. The cluster generator 202 receives, as inputs, one or more factors 204 and one or more profiles 206 and generates one or more clusters 208 based on the combination of factors 204 and profiles 206. The factors, or variables, 204 include different factors for a particular condition, such as menopause, including symptoms associated with different stages of menopause. For example, various factors may include age, ethnicity, health history, symptoms, medications, exercise regimen, environmental factors, and so forth. Each profile 206 includes data related to each factor 204 for the particular consumer associated with the profile 206. For example, each profile 206 includes consumer data related to the age of the consumer, ethnicity of the consumer, historical symptoms of the consumer, current symptoms of the consumer, and so forth.

The cluster generator 202 implements a clustering algorithm to determine the similarity between a particular profile and each additional profile. In some examples, a profile is added to a particular cluster, or a new cluster is generated, when the profile has a similarity threshold with the other profiles that are included in the cluster that reaches or exceeds a similarity threshold. The similarity threshold may be a threshold percentage of data values of the profiles that are the same or similar, a threshold number of the data values that are the same, one or more particular values that are the same, or any other suitable threshold for determining similarity.

In examples where the cluster generator 202 initially generates clusters, the cluster generator 202 identifies one or more identifying features of a persona of the cluster. The persona is an artificial profile that represents the data values of the profiles in the cluster. For example, a persona for a first cluster includes women ages 50-54 that are in the menopause stage. The cluster generator 202 identifies profiles that match aspects of the persona and then separates those profiles into one or more clusters based on additional factors. In this example, a first cluster **208*a* is generated for profiles of women ages 50-54 in the menopause stage with symptoms that are self-characterized as "mild", a second cluster 208*b* is generated for profiles of women ages 50-54 in the menopause stage with symptoms that are self-characterized as "average", and a third cluster 208*n* is generated for profiles of women ages 50-54 in the menopause stage with symptoms that are self-characterized as "severe". A first persona 210 is associated with the first cluster 208***a*, a second persona 212 is associated with the second cluster 208*b*, and a third persona 214 is associated with the third cluster 208*n*. It should be understood that the present example is presented for illustration only. In various examples, various clusters are generated based on a variety of different factors without departing from the scope of the present disclosure.

Accordingly, the architectural structure of the clusters 208 and personas 210-214 provide an improved set of indexes that are stored in the data storage device 114 that facilitate improved retrieval by one or more elements of the recommendation engine 124. Improving the retrieval of data associated with one or more clusters 208 and/or one or more personas 210-214 enables more effective association of a new profile with an existing cluster as well as more effective re-association of an existing profile with a different cluster based on new data being received. The retrieval of the data is improved by storing the clusters 208, i.e., the clusters 118, in the data storage device 114 with the associated personas 210-214 embedded with the clusters 208, which reduces the consumption of computing resources required to associate an updated profile with a new cluster. Clusters 208 may be stored with in the data storage device 114 with tags indicating similarities between different clusters 208 so that the cluster generator 202 may identify a new cluster, or set of new clusters, with a high probability for an updated profile to be associated with. This in turn enables the cluster generator 122 to learn, over time, that particular changes to profiles in a particular cluster 208 historically lead to the profile being associated with a particular new cluster. This results in a reduced consumption of computing resources for associating an existing profile with a new cluster based on new data being received.

In examples where the cluster generator 202 receives a new or updated profile to include in an existing cluster, the cluster generator 202 executes a clustering algorithm to compare the received profile to other profiles in different clusters. In some examples, the profile is added to the cluster with which the received profile has the highest similarity score. In other examples, the highest similarity score is compared to a similarity threshold to determine whether the profile is similar enough to the profiles of the closest cluster to be included in the cluster. Where the similarity score is equal to or exceeds the similarity threshold, the profile is added to the cluster. Where the similarity score is less than the similarity threshold, the profile is not similar enough to the profiles in the cluster to be included and the cluster generator 202 generates a new cluster for the profile.

In some examples, the cluster generator 202 implements a two-stage process to strategically prune a feature space for biological features, given that data may include a high variety of features, some of which are highly correlated with a particular condition, such as menopause, and others which are less associated with the particular condition. The two-stage process includes i) a hierarchical feature collapse, and ii) a selection of top features by performing a principal component analysis (PCA). In the hierarchical feature collapse, the cluster generator 202 groups features together are more similar to one another, reflecting the strength of similarity between the features on a vertical axis. The number of resulting feature clusters is determined based on where the threshold on the vertical axis is cut. Features with a maximum variance are taken in the scenario where there are multiple elements in the feature cluster. In some examples, a more aggressive threshold is taken to further collapse the feature space. In other examples, a more conservative threshold is taken so as to only eliminate highly redundant features.

PCA is an unsupervised machine learning method to partition the variability in the data on non-overlapping axes consisting of linear combinations of the features such that the first few axes account for the most variability. The data is normalized by centering and scaling the data, which improves how informative the PCA. Otherwise, some features on a larger scale may dominate the axes. In some examples, a first number of features, such as the first then features in the first three principal components, are selected to identify the top features.

In some examples, the clusters generated by the cluster generator 202 are generated and output as a visualization, such as a heatmap. For visualization of the clusters, the biological dataset is scaled by a maximum feature importance for each of the features across the first three principal components. This effectively weights the raw data by the amount of variability the feature accounts for in the biological dataset and thus provides a better visual representation. In some examples, the clusters are visualized as clouds of like individuals as opposed to discrete clusters, given the continuous nature of the biological data. In some examples, an additional model is used to further cluster the data. For example, a partition around medoids (PAM) may be selected, which is robust to outliers, stable, fast, and capable of handling different data types. Various performance metrics, such as the Silhouette index, Calinski-Harabasz, or any other suitable clustering performance metrics, may be used to determine cluster size. As the biology underlying menopause is continuous, literal interpretation of these discrete clustering metrics is inappropriate. Instead, using them as guidelines for a range of k may provide more informative clustering and analysis. The choice of k is determined based on a balance between visually inspecting the plots of these metrics over k and marketing bandwidth for menopausal personalization. The generated heatmap may then display the features by cluster, where color intensity corresponds to more extreme values, a first color corresponds to higher values, and a second color corresponds to lower values.

In summary, the cluster generator 202 performs the clustering by performing a hierarchical feature collapse to remove redundant features, taking top PCA features as selected features, scaling the PCA visualization by weights of top features, applying an additional model, such as PAM, to cluster the scaled data of selected features, choosing a value k by using various performance metrics such as the Silhouette index, Calinski-Harabasz, or other marketing resource constraints, and re-clustering with an optimal k value and using the cluster labels for analysis.

In some examples, certain biological features, also referred to herein as inclusion features, are included in the feature space utilized by the cluster generator 202 due to healthcare providers or practitioners considering them particularly pertinent to the particular condition or removed from the feature space utilized by the cluster generator 202 due to healthcare providers or practitioners considering them not particularly relevant to the particular condition. In some examples, the biological feature model includes upweighted features to emphasize a particular feature or features.

In some examples, the cluster generator 202 further clusters behavior determined to relate specifically to the particular condition in question, such as menopause. To do so, the cluster generator 202 i) correlates biological and behavior features, ii) for each mapped biological feature, identifies behavioral features that map to the biological feature above a set threshold, iii) uses the highest mapped behaviors for a cluster, and iv) applies the clustering process described herein for the various factors except for the behavioral feature collapse, as feature filtering has already been performed. For example, the cluster generator 202 correlates the biological and behavioral features and identifies which behavioral features have the highest correlations to biological features, which then serve as reasonable proxies for underlying menopausal symptoms. The heatmap of the correlation between biological and behavioral features shows that the behavioral features are meaningfully clustered by the biology. In other words, there are clear groupings of behavioral questions/themes, which provides positive feedback of the clustering approach. Although in some examples the absolute correlation between the biological and behavioral features may be relatively low, this signal is meaningful as real-world correlations, particularly with humans, tend to be much weaker and harder to measure than lab controlled experiments.

In some examples, the behavioral model is combined with the biological model to develop a single model that models the dependence of the biological and behavioral features. In this example, a lighter hierarchical feature collapse is performed, as the feature space dramatically expands with the feature union. Using this reduced feature set, the same set of clustering procedures are performed as discussed herein, with the exception of the PCA feature selection stage, which is performed separately in the individual models.

Figure 3:
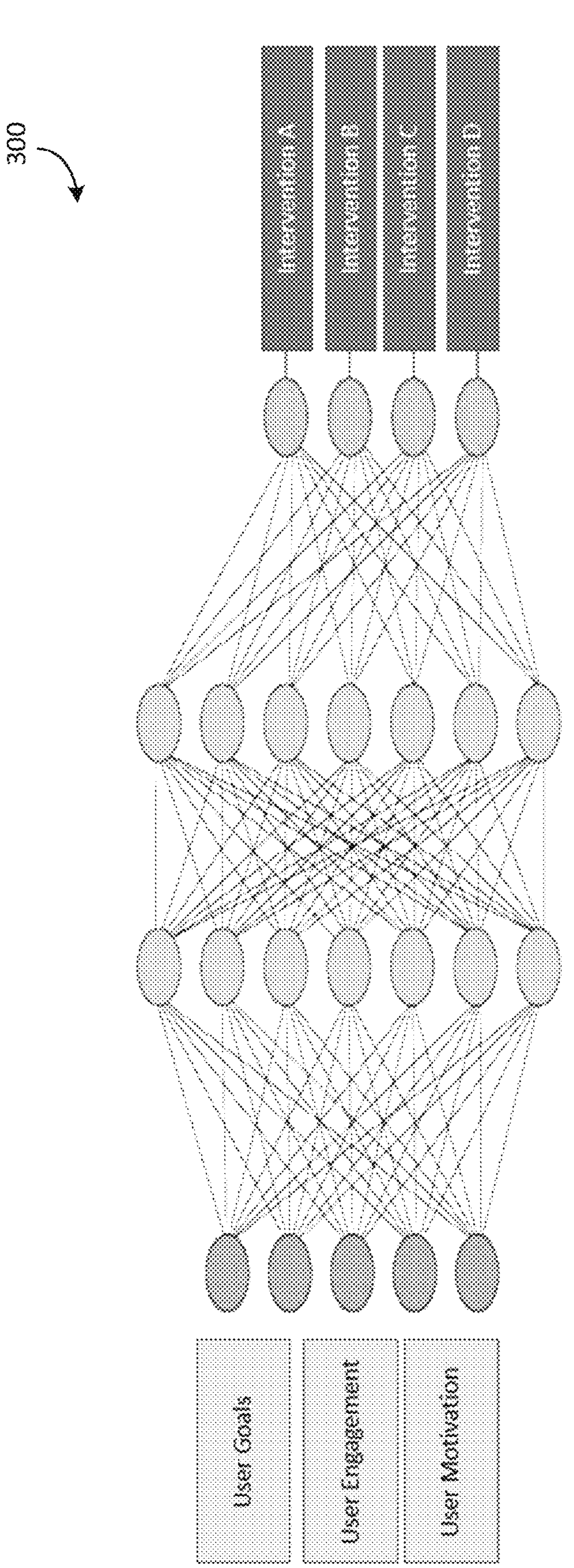
FIG. 3 illustrates an example of a recommendation engine for generating interventions for a particular profile.

FIG. 3 illustrates an example of a recommendation engine for generating interventions for a particular profile. The example recommendation engine 124 illustrated in FIG. 3 is for illustration only and should not be construed as limiting. Various examples of the recommendation engine 124 may be implemented without departing from the scope of the present disclosure.

As described herein, the recommendation engine 124 generates one or more recommendations based on the consumer profile and/or the cluster to which the consumer profile belongs. FIG. 3 illustrates examples of inputs received by the recommendation engine 124 in addition to the factors 204 for a particular profile 206 that are used to generate one or more recommended interventions for a particular profile. For example, various examples of inputs the recommendation engine 124 receives and uses include, but are not limited to, user goals, user engagement, and user motivation. User goals are examples of what a user wants to accomplish. For examples, user goals may include receiving as much educational content as possible, receiving a set amount of educational content, mitigating symptoms, and so forth. User engagement refers to a user's historical and/or anticipated engagement with the system 100, such as a likelihood that a consumer will implement generated recommendations, provide feedback regarding implemented recommendations, and so forth. User motivation refers to a reasoning why the consumer initially engaged and/or continues to engage the system 100. User motivation arises from a psychological profile of an individual. For example, a target goal may be provided but depending on the user motivation, this goal may or may not be expected to be achieved. Where a user's underlying motivations are understood, different products may be recommended based on the ability of a user, or anticipated ability of a user, to adhere to.

Based on the received inputs, the recommendation engine 124 generates a recommendation that includes at least one intervention, such as intervention A, intervention B, intervention C, intervention D, and so forth that, when implemented, addresses an anticipated health outcome for the consumer. As described herein, an intervention include a product, a combination of two or more products, a lifestyle adjustment, a combination of two or more lifestyle adjustments, a combination of at least one product and at least one lifestyle adjustment, and so forth.

Figure 4:
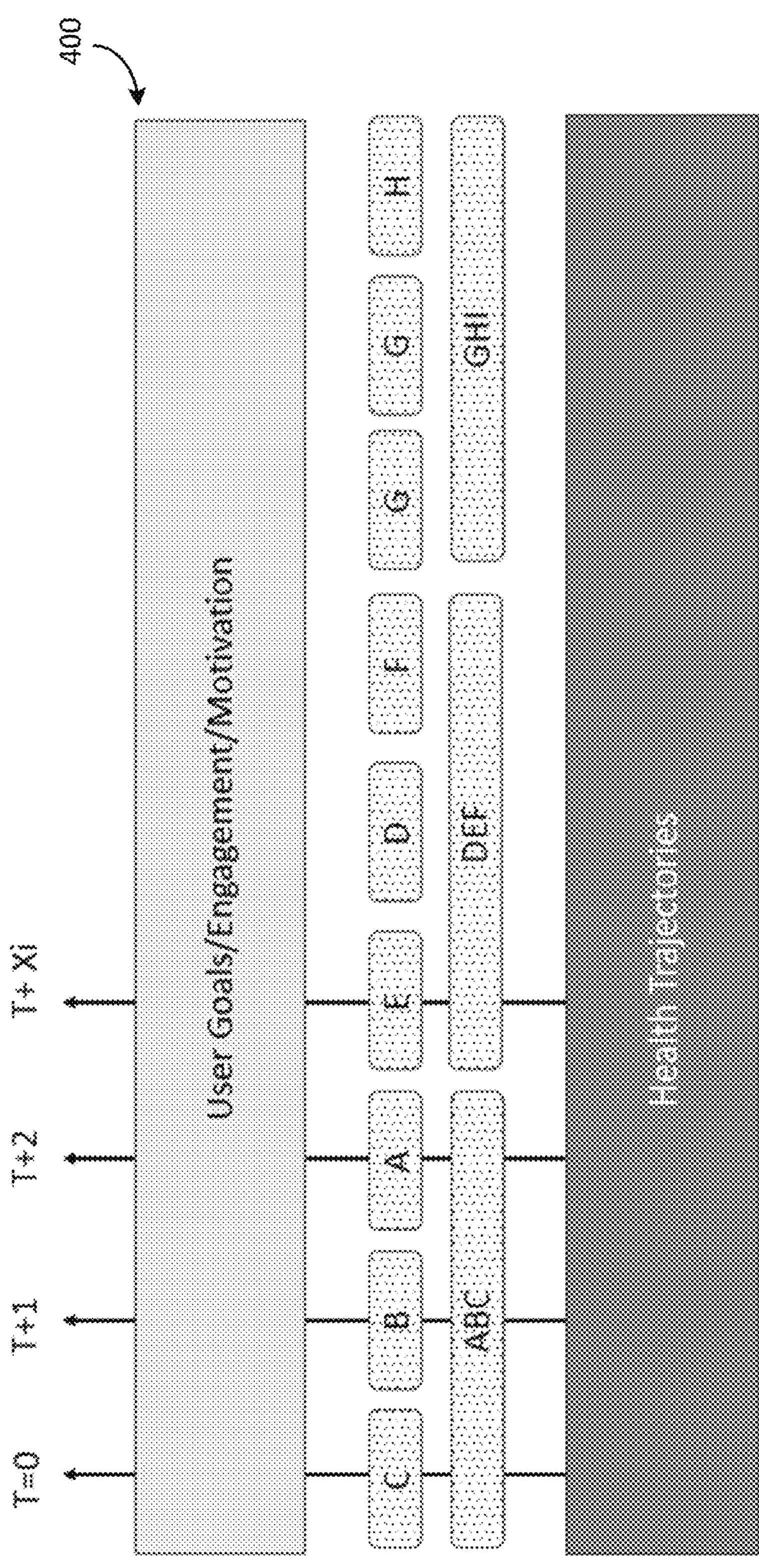
FIG. 4 illustrates an example timeline of a profile updating over time.

FIG. 4 illustrates an example timeline of a profile updating over time. The example timeline 400 illustrated in FIG. 4 is provided for illustration only and should not be construed as limiting. Various examples of the timeline 400 may be implemented without departing from the scope of the present disclosure.

The timeline 400 illustrates a combination of health trajectories, user goals, engagement, and motivation, rankings, and models over time. As time progresses, a consumer's goals, engagement, and motivation, rankings may change. In addition, the cluster in which the profile of the consumer is placed may change based on the consumer's changing age, updates to the consumer's profile such as an symptoms increasing or decreasing over time, whether or not a recommended intervention or interventions has been implemented, and so forth.

As shown in FIG. 4, at an initial time, T=0, the consumer has a ranking of C and a particular recommendation model ABC is implemented to generate a recommendation. At a second time, T+1, as the consumer goals change, the consumer has an updated ranking of B, but the recommendation model ABC is still implemented to generate the recommendation. Additional changes are shown at additional times T=2 and T=Xi.

Figure 5:
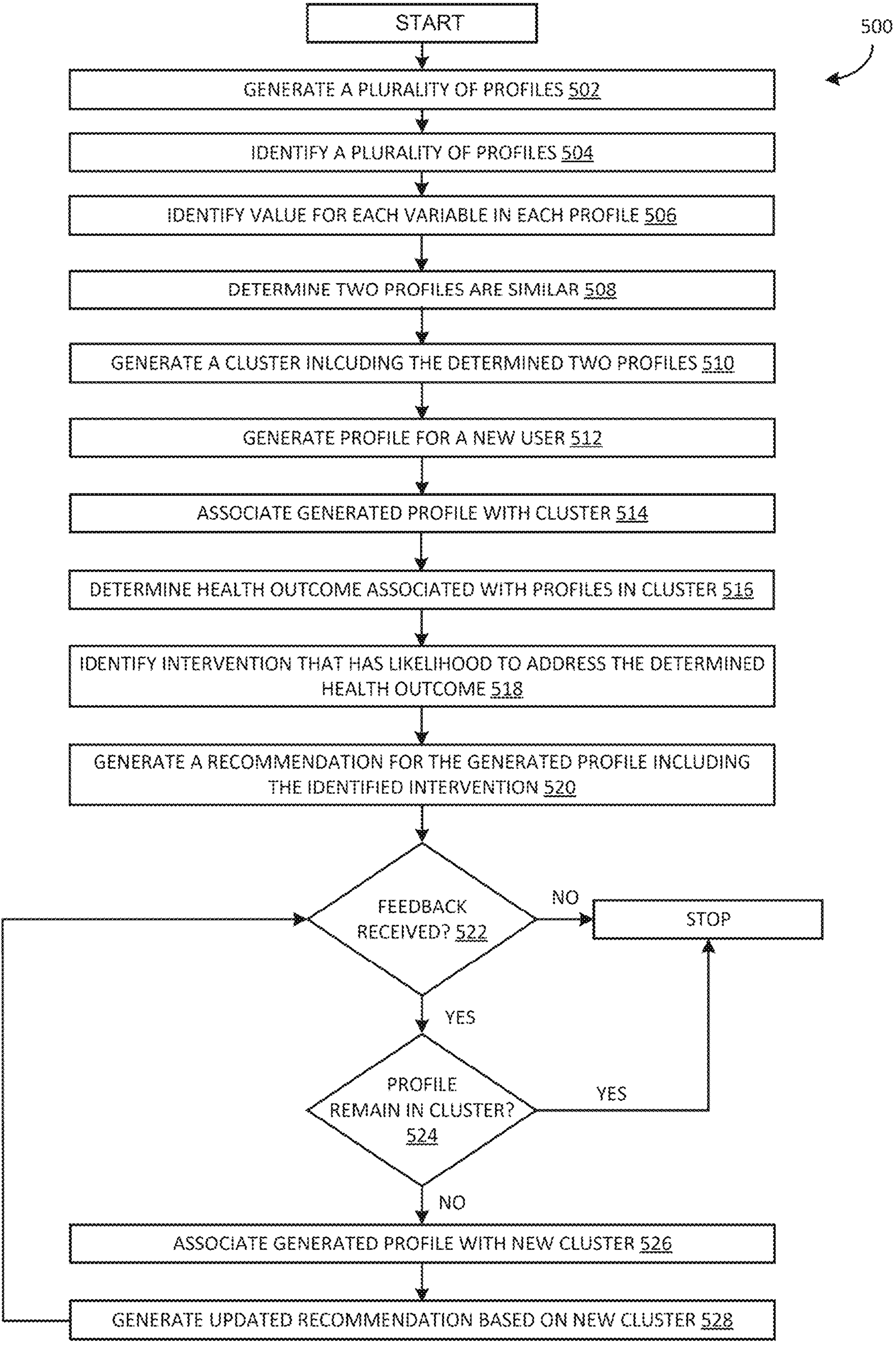
FIG. 5 illustrates an example computer-implemented method of generating one or more recommendations for a profile.

FIG. 5 illustrates an example computer-implemented method of generating one or more recommendations for a profile. The computer-implemented method 500 is presented for illustration only and should not be construed as limiting. Other examples of the computer-implemented method 500 can be used without departing from the scope of the present disclosure. The computer-implemented method 500 can be implemented by one or more electronic devices described herein, such as the computing device 102.

The computer-implemented method 500 begins by the profile generator 120 generating a plurality of profiles 116 in operation 502. As described herein, the profile generator 120 generates a separate profile 116 for each respective consumer based on data received from the consumer, such as data input on the external device 140 and transmitted to the computing device 102. Each newly generated profile 116 is stored in the data storage device 114.

In operation 504, the cluster generator 122 identifies a plurality of generated profiles 116. In some examples, the cluster generator 122 identifies the plurality of generated profiles 116 automatically as the profile is generated. In other examples, the cluster generator 122 identifies the plurality of generated profiles 116 in response to a trigger event, such as a time of day occurring. For example, the cluster generator 122 identifies the plurality of generated profiles 116 at a regular interval, such as the same time each day, once a week, once every two weeks, and so forth.

In operation 506, the cluster generator 122 identifies a value for each variable in each profile 116. As described herein, variables for the consumer include, but are not limited to, age, ethnicity, income, geographical location, awareness of menopause, various menopause-related symptoms, and so forth. A value is a value of a particular variable. For example, a value for the variable of age includes the numerical age of the consumer.

In operation 508, the cluster generator 122 determines that two profiles 116 are similar. In some examples, the cluster generator 202 implements a clustering algorithm to determine the similarity between a particular profile and each additional profile. For example, the cluster generator 202 identifies one or more identifying features of a persona of the cluster. The cluster generator 202 then identifies profiles that match aspects of the persona and then separates those profiles into one or more clusters based on additional factors. In operation 510, generates the cluster 118 including the determined two profiles 116. The generated cluster 118 is stored in the data storage device 114.

In operation 512, the profile generator 120 generates a new profile for a new user. For example, the profile generator 120 generates a new profile for a consumer based on information received from the consumer indicating personal variables. The newly generated profile 116 is stored in the data storage device 114.

In operation 514, the cluster generator 122 associates the newly generated profile 116 with an existing cluster 118. For example, the cluster generator 202 executes a clustering algorithm to compare the received profile to other profiles in different clusters. In some examples, the profile is added to the cluster with which the received profile has the highest similarity score. In other examples, the highest similarity score is compared to a similarity threshold to determine whether the profile is similar enough to the profiles of the closest cluster to be included in the cluster. Where the similarity score is equal to or exceeds the similarity threshold, the profile is added to the cluster. Where the similarity score is less than the similarity threshold, the profile is not similar enough to the profiles in the cluster to be included and the cluster generator 202 generates a new cluster for the profile. The cluster 118 is updated in the data storage device 114 to include the newly generated profile 116.

In operation 516, the health outcome identifier 126 identifies a health outcome associated with the cluster 118 in which the newly generated profile 116 was included. In some examples, the health outcome includes a stage of menopause for the user associated with the profile based on the received information. In some examples, the identified health outcomes are stored as a value of the cluster 118 in the data storage device 114.

In operation 518, the intervention identifier 128 identifies an intervention that has a likelihood to address the determined health outcome. For example, the intervention identifier 128 identifies a particular intervention that, when applied, are anticipated to alleviate or mitigate symptoms associated with the identified phase of menopause and the most severe symptoms identified by the user based on research data, clinical data, and so forth. Various examples of an intervention include a product, a combination of two or more products, a lifestyle adjustment, a combination of two or more lifestyle adjustments, a combination of at least one product and at least one lifestyle adjustment, and so forth. In some examples, the identified intervention includes educational content associated with at least one of the identified phase of menopause or the identified symptoms of the user. In some examples, the interventions are stored in the data storage device 114 as interventions 119 crossed reference with health outcomes.

In operation 520, the recommendation generator 130 generates a recommendation for the profile 116, including the identified intervention 119. The generated recommendation includes the intervention 119 identified by the intervention identifier 128 and instructions for implementation of the identified intervention 119. In some examples, an intervention includes a particular product, educational content, and a lifestyle adjustment. The generated recommendation includes instructions for implementing the intervention.

In operation 522, the feedback receiver 132 determines whether feedback has been received regarding the generated and presented recommendation. Received feedback may include one or more indications regarding the success, failure, and/or viability of the generated recommendation, and/or the value of the educational content that was delivered. In some examples, feedback is received through the completion of a user survey, where a consumer provides scaled ratings for various elements of the recommendation, such as a scale of one to ten, one to five, and so forth. In other examples, feedback is received based on user data that maps whether the recommended product was purchased through the provided link, whether the recommended product was purchased at a later time, whether the recommended product was purchased multiple times, and so forth. In examples where feedback is not received, the computer-implemented method 500 terminates.

In examples where feedback is received, in operation 524 the cluster generator 122 analyzes the received feedback and determines whether changes to the profile 116 result in the profile 116 remaining in the cluster 118. For example, the cluster generator 122 repeats the process described in operation 514 and then determines whether the profile 116 is still most similar to the initial cluster 118 or a new cluster 118. In examples where the changes to the profile 116 do not result in a significant enough change for the profile to move to a different cluster, i.e., the profile 116 remains in the same cluster 118, the computer-implemented method 500 terminates. In examples where the changes to the profile 116 do result in a significant enough change for the profile to move to a different cluster, the computer-implemented method 500 proceeds to operation 526 and the cluster generator 122 associates the profile with a new cluster 118. Then, in operation 528, the recommendation generator 130 generates an updated recommendation for the profile 116 based on the profile 116 being associated with the new cluster 118. The updated recommendation is presented to the consumer, such as via the user device 140, and the computer-implemented method 500 returns to operation 522 to determine whether feedback is received regarding the updated recommendation.

Figure 6:
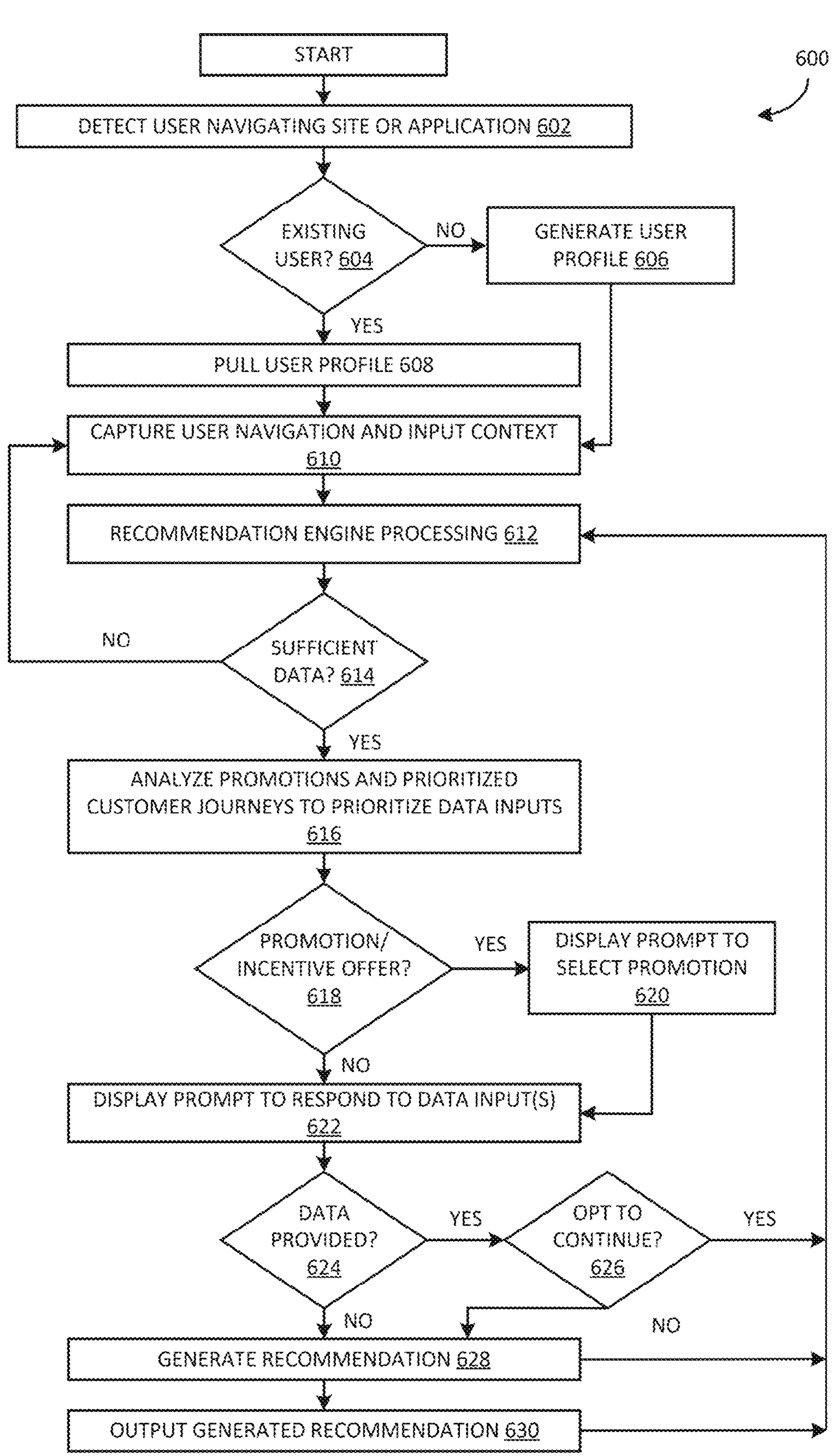
FIG. 6 illustrates an example computer-implemented method of generating one or more recommendations for a profile.

FIG. 6 illustrates an example computer-implemented method of generating one or more recommendations for a profile. The computer-implemented method 600 is presented for illustration only and should not be construed as limiting. Other examples of the computer-implemented method 600 can be used without departing from the scope of the present disclosure. The computer-implemented method 600 can be implemented by one or more electronic devices described herein, such as the computing device 102.

The computer-implemented method 600 begins by the user interface device 110 or the user interface device 148 detecting user navigation on an application 107 or application 154, respectively, in operation 602. The user navigation on the application 107 or application 154 may be a mobile application, a web-based application, or any other suitable type of hosted application. In some examples, the detected user navigation includes detecting an input to the user interface device 110 or the user interface device 148, responding to a prompt presented on the user interface device 110 or the user interface device 148, and so forth.

In operation 604, the profile generator 120 determines whether the user navigating the site in operation 602 is an existing user. In some examples, the profile generator 120 determines whether the user is an existing user based on data obtained from the user device being used to navigate the site. For example, the application 107 or application 154 may determine whether a user is logged in to the application 107 or application 154, capture internet protocol (IP) data from the user device and compare the IP data to IP data of existing users, or any other suitable data to determine whether the user is an existing user. In examples where the user is not determined to be an existing user, the method 600 proceeds to operation 606 where the profile generator 120 generates a new profile for the new user. In examples where the user is not determined to be an existing user, the method 600 proceeds to operation 608 where the profile generator 120 pulls the user profile. For example, the user profile and associated data are stored as data 116 in the data storage device 114, and the profile generator 120 pulls the user profile and associated data.

In operation 610, following either the generation of a user profile in operation 606 or retrieval of the user profile in operation 608, the application 107 or application 154 captures user navigation and input context via the user interface device 110 or the user interface device 148, respectively. The application 107 or the application 154 captures user navigation and input context including, but not limited to, items selected by the user, items viewed by the user, data input to the application 107 or application 154 by the user, and so forth.

In operation 612, the recommendation engine 124 executes one or more processing actions. In some examples, this includes one or more of the health outcome identifier 126 identifying, or predicting, a stage of menopause for the user based on the inputs received, the intervention identifier 128 identifying an intervention, and the recommendation generator 130 generating a recommendation for the user. In some examples, concurrent processing is performed for current needs, i.e., recommendations to be presented to the user while they are navigating the site, as well as for future needs, i.e., to improve future recommendations to the user or other users.

In operation 614, the recommendation engine 124 determines whether sufficient data is available for the recommendation generator 130 to generate a sufficiently robust recommendation, including one or more identified interventions. In some examples, the recommendation engine 124 requires a threshold amount of data to be available in order to generate a recommendation anticipated to be accurate for the user. If sufficient data is not available, in operation 614 the recommendation engine 124 determines the sufficient amount of data is not available, identifies what additional data would be beneficial for current recommendation and future simulations, and the method 600 returns to operation 610 to capture additional user navigation and input context in order to gather the needed data. For example, sufficient data may not be available in the instance such as where, in operation 604, the user was not existing and the user has not provided enough inputs to gather sufficient data.

Where sufficient data is available, in operation 616 the recommendation generator 130 analyzes available promotions and a prioritized customer journey to prioritize data inputs within the application 107 or application 154. For example, a promotion may be presented to incentivize participation where needed and drive the input of additional responses to prompts by a user. Examples of available promotions and prioritized customer journeys include, but are not limited to, a discounted purchase, free samples, early access to a new product, and so forth. Data inputs are prioritized to include those which facilitate additional data for the training of one or more aspects of the recommendation engine 124, additional data that is needed for an improved recommendation to be generated and presented to the user, and so forth.

In operation 618, the recommendation generator 130 determines whether a promotion or incentive offer is available. Where a promotion is identified and determined to be available, the method 600 proceeds to operation 620 where the user interface device 110 or the user interface device 148 displays a prompt that, when selected by the user, selects the identified promotion. Where a promotion is not determined to be available, or following the prompt being displayed in operation 620, the method 600 proceeds to operation 622 and the user interface device 110 or the user interface device 148 displays a prompt that, when selected by the user, responds to one or more data inputs. For example, where a promotion is unavailable, the user interface device 110 or the user interface device 148 may present a prompt that, when selected, indicates whether the user is open or not open to sharing the data.

In operation 624, the recommendation generator 130 determines whether data has been provided, by the user, in response to the prompt displayed on the user interface device 110 or the user interface device 148. Where data has been provided, the method 600 proceeds to operation 626 and the recommendation generator 130 determines whether the provided data indicates the user opts to continue and receive a recommendation. Where the user has opted to continue and allow their data to be used, the method 600 returns to operation 612, where the recommendation engine 124 continues to process, which is now performed with the inclusion of the user data. Where the user has not opted to continue and allow their data to be used in operation 626, or if the data is not provided in operation 624, in operation 628 the recommendation generator 130 generates a recommendation for the user as described herein. The generated recommendation is then output and displayed on the user interface device 110 or the user interface device 148 in operation 630. Following the generated recommendation being output, the method 600 returns to operation 612 and continues processing.

As illustrated in the computer-implemented method 600 illustrated in FIG. 6, sufficient data quality and volume are needed to achieve meaningful recommendation/guidance. In some examples, the datasets needed to generate the actions that can drive an intended outcome may not already exist. The computer-implemented method 600 operates to create a feedback loop where one or more base models are implemented with active customer engagement via simple prompts to the customer. In some examples, promotions are used to incentivize participation where needed. The computer-implemented method 600 accounts for data elements with the highest impact on accuracy and prioritizes those data elements to increase data collection in those areas that a) most influence the model and b) lead to the most accurate results for that individual customer. Where no input is provided or data is not present to drive the best results of a model a default profile is used based on the limitations of the dataset. Many interactions of this type rely on customers to initially engage with follow up from the digital platform. This approach is to pro-actively engage customers via very light and quick prompts during natural navigation of the site based on events within that progression. The combination of these two approaches increases the reach and reduces the barriers to engagement.

In addition, this approach also allows for collection of both anonymous and named customer data, if prior consent is obtained and available, with the ability to segment those two datasets. Traditionally, these types of approaches rely on named customer data, which creates additional barriers to reaching the full target audience, as well as increases the exposure and collection of significant data to accelerate early findings and patterns which can then inform and drive different approaches to further study or analyze those patterns. Accordingly, the present disclosure recognizes and takes into account these challenges and provided segmented datasets, increasing the ability of the one or more models to be trained on and execute captured data. In some examples, improvements in recommendations provided directly to a user, as well as anticipation of future progression of symptoms or needs, significantly improves customer satisfaction and increase customer loyalty. Data collected informs the model targeted for the individual with more accurate results but also generally improves for the larger community in the given space.

FIGS. 7A-7G illustrate example user interfaces (UIs) of a flow including creating a profile, receiving data, and generating a recommendation. The example UIs illustrated in FIGS. 7A-7G are provided for illustration only and should not be construed as limiting. Various examples may be used without departing from the scope of the present disclosure. In some examples, the example UIs illustrated in FIGS. 7A-7G are examples of the user interface device 148 illustrated in FIG. 1 presenting a client-side application 154. In some examples, the example UIs illustrated in FIGS. 7A-7G are UIs for an application 154 focused on providing resources and support for women experiencing menopause.

Figure 7A:

FIG. 7A illustrates a first UI 701. The first UI 701 is an example of a landing page of the application 154 that introduces the application 154 and provides a consumer with information regarding the application 154. For example, the first UI 701 includes information regarding a first step, at which the UI 701 receives one or more inputs specifying a goal for a consumer of using the application 154.

Figure 7B:
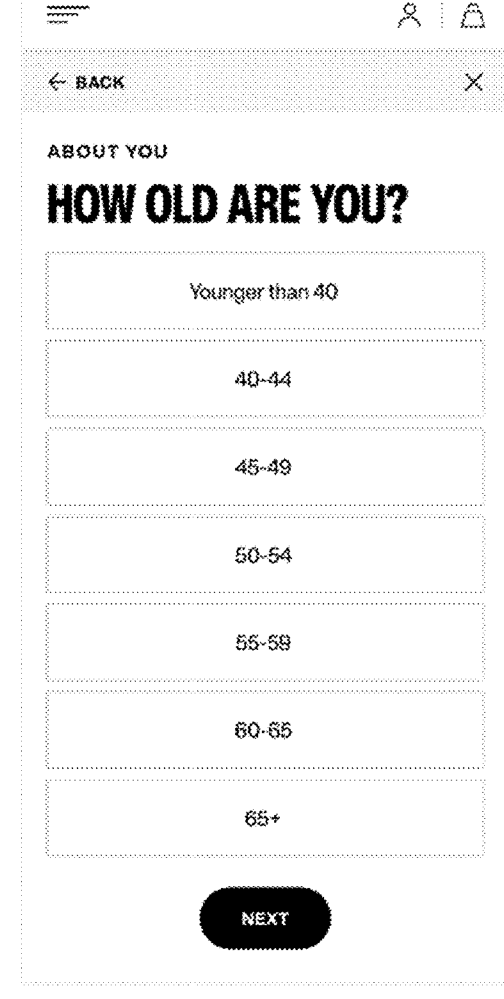

FIG. 7B illustrates a second UI 702. The second UI 702 is an example of a portion of a holistic assessment of the consumer and illustrates selectable icons that, when selected, provide a response to a section of a questionnaire. In particular, the second UI 702 illustrates an example selection of different age ranges of the consumer, including "Younger than 40", "40-44", "45-49", and so forth.

Figures 7C, 7D:
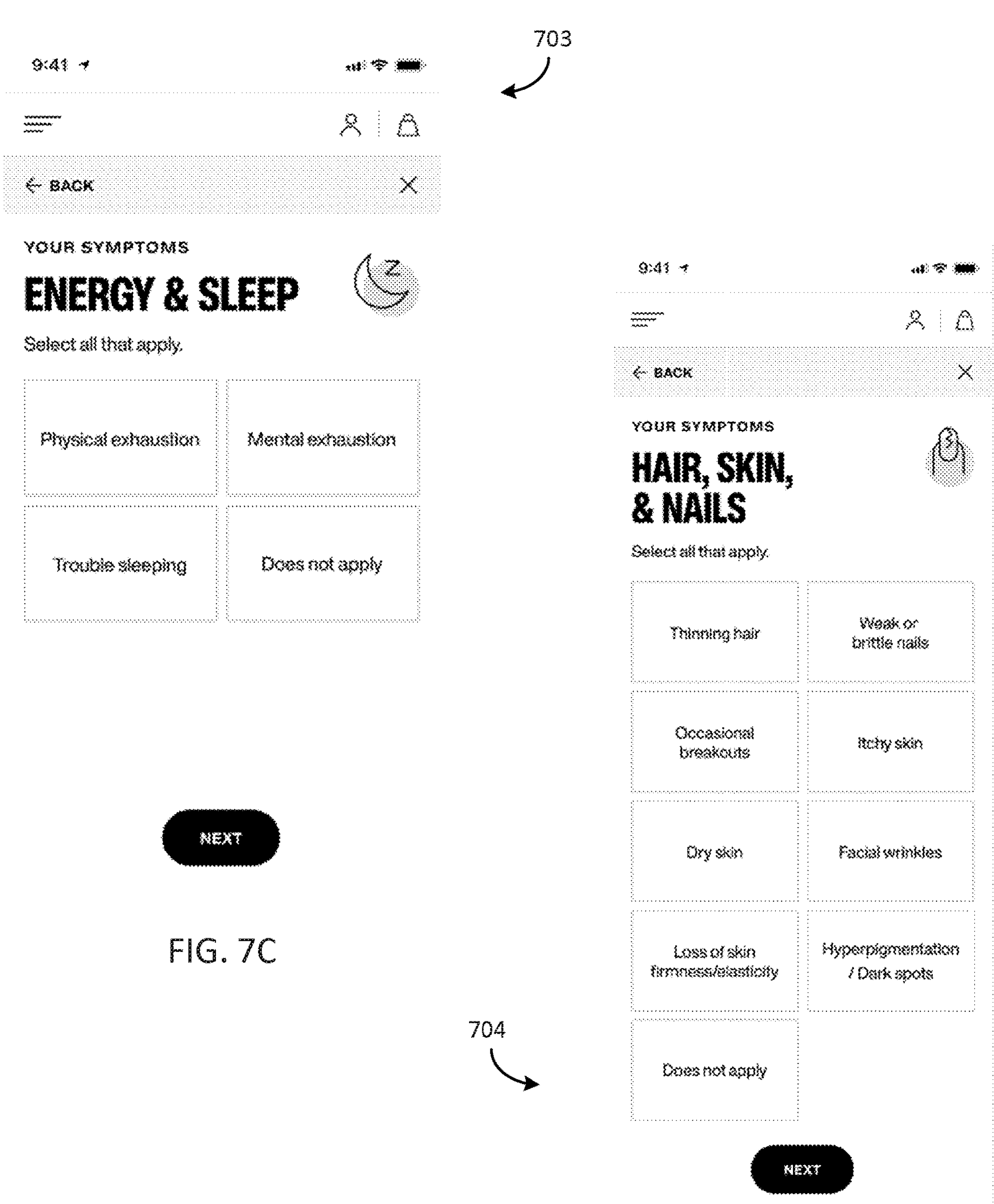

FIG. 7C illustrates a third UI 703 that includes another aspect of the questionnaire. For example, the third UI 703 illustrates an example question of the questionnaire regarding a consumer's energy and sleep, with multiple selectable options representing different symptoms of menopause related to energy and sleep. FIG. 7D illustrates a fourth UI 704 that includes yet another aspect of the questionnaire, such as an example question regarding a consumer's hair, skin, and nails, with multiple selectable options representing different symptoms of menopause related to hair, skin, and nails. Although FIGS. 7C and 7D illustrate two examples of questions regarding menopause symptoms, various examples are possible. Various other questions may be include, but are not limited, questions regarding symptoms related to age, ethnicity, energy and sleep, mood and mind, hot flashes, intimacy, weight changes, digestion, bone health, headaches, muscle and joint pain, and so forth.

FIG. 7E illustrates a fifth UI 705 that includes a section for a consumer to input identifying information, such as a first name and email address. The provided email address is used to provide the consumer with recommendations based on their responses to the questions in the questionnaire, as well as to identify the consumer when logging in to the application 154 to monitor and track the progression of symptoms over time in order to provide updated recommendations. FIG. 7F illustrates a sixth UI 706 that includes a description of a stage of menopause based on the provided responses to the questions in the questionnaire. In some examples, the determined stage is based on the age or age range provided. In other examples, the determined stage is based on the responses to one or more questions in the questionnaire.

Figure 7G:
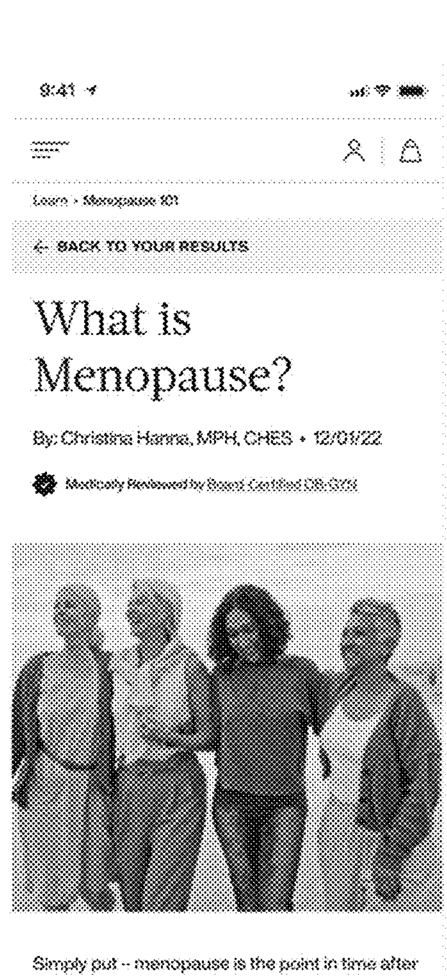

FIG. 7G illustrates a seventh UI 707 that presents a generated recommendation based on the determined stage of menopause of the consumer and the identified symptoms provided in the responses to the questions of the questionnaire. In some examples, the generated recommendation is based on the highest ranked symptom identified, such as the symptom the consumer considers to be the most serious, the symptom the consumer is determined to be most the likely to seek treatment or relief from, and so forth. The generated recommendation includes one or more of a resource such as an article or video that provides education and/or suggested treatment for a particular symptom, a product that can be used to reduce or alleviate a symptom, a list of medical professionals available for a medical visit via an in-person appointment or telehealth appointment, and so forth.

Example Operating Environment

Figure 8:
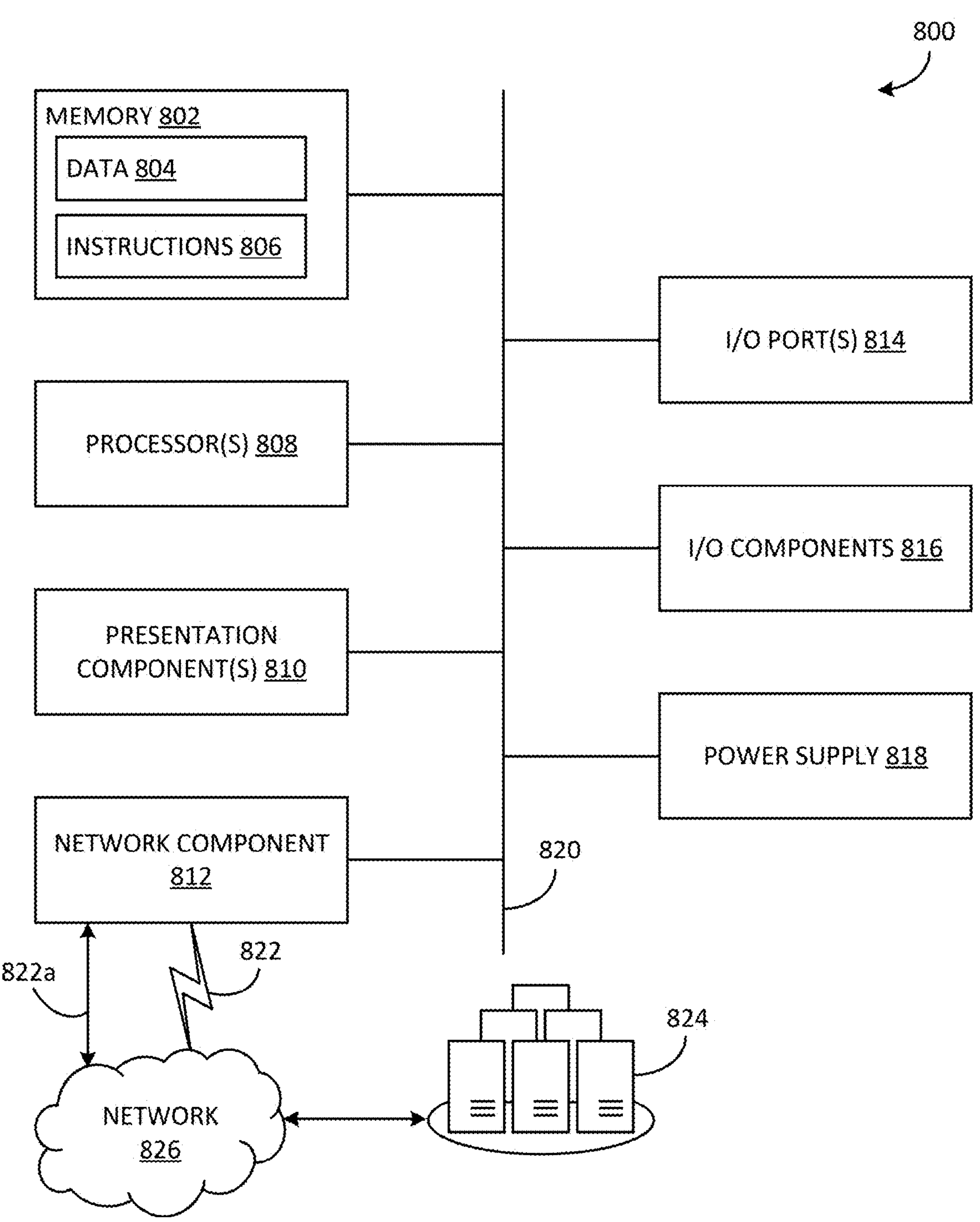
FIG. 8 is a block diagram illustrating an example computing environment suitable for implementing one or more of the various examples disclosed herein.

FIG. 8 is a block diagram of an example computing device 800 for implementing aspects disclosed herein and is designated generally as computing device 800. Computing device 800 is an example of a suitable computing environment and is not intended to suggest any limitation as to the scope of use or functionality of the examples disclosed herein. Neither should computing device 800 be interpreted as having any dependency or requirement relating to any one or combination of components/modules illustrated. The examples disclosed herein may be described in the general context of computer code or machine-useable instructions, including computer-executable instructions such as program components, being executed by a computer or other machine, such as a personal data assistant or other handheld device. Generally, program components including routines, programs, objects, components, data structures, and the like, refer to code that performs particular tasks, or implement particular abstract data types. The disclosed examples may be practiced in a variety of system configurations, including personal computers, laptops, smart phones, mobile tablets, hand-held devices, consumer electronics, specialty computing devices, etc. The disclosed examples may also be practiced in distributed computing environments when tasks are performed by remote-processing devices that are linked through a communications network.

Computing device 800 includes a bus 820 that directly or indirectly couples the following devices: computer-storage memory 802, one or more processors 808, one or more presentation components 810, I/O ports 814, I/O components 816, a power supply 818, and a network component 812. While computing device 800 is depicted as a seemingly single device, multiple computing devices 800 may work together and share the depicted device resources. For example, memory 802 may be distributed across multiple devices, and processor(s) 808 may be housed with different devices.

Bus 820 represents what may be one or more busses (such as an address bus, data bus, or a combination thereof). Although the various blocks of FIG. 8 are shown with lines for the sake of clarity, delineating various components may be accomplished with alternative representations. For example, a presentation component such as a display device is an I/O component in some examples, and some examples of processors have their own memory. Distinction is not made between such categories as "workstation," "server," "laptop," "hand-held device," etc., as all are contemplated within the scope of FIG. 8 and the references herein to a "computing device." Memory 802 may take the form of the computer-storage media references below and operatively provide storage of computer-readable instructions, data structures, program modules and other data for computing device 800. In some examples, memory 802 stores one or more of an operating system, a universal application platform, or other program modules and program data. Memory 802 is thus able to store and access data 804 and instructions 806 that are executable by processor 808 and configured to carry out the various operations disclosed herein.

In some examples, memory 802 includes computer-storage media in the form of volatile and/or nonvolatile memory, removable or non-removable memory, data disks in virtual environments, or a combination thereof. Memory 802 may include any quantity of memory associated with or accessible by computing device 800. Memory 802 may be internal to computing device 800 (as shown in FIG. 8), external to computing device 800, or both. Examples of memory 802 in include, without limitation, random access memory (RAM); read only memory (ROM); electronically erasable programmable read only memory (EEPROM); flash memory or other memory technologies; CD-ROM, digital versatile disks (DVDs) or other optical or holographic media; magnetic cassettes, magnetic tape, magnetic disk storage or other magnetic storage devices; memory wired into an analog computing device; or any other medium for encoding desired information and for access by computing device 800. Additionally, or alternatively, memory 802 may be distributed across multiple computing devices 800, for example, in a virtualized environment in which instruction processing is carried out on multiple computing devices 800. For the purposes of this disclosure, "computer storage media," "computer-storage memory," "memory," and "memory devices" are synonymous terms for computer-storage memory 802, and none of these terms include carrier waves or propagating signaling.

Processor(s) 808 may include any quantity of processing units that read data from various entities, such as memory 802 or I/O components 816 and may include CPUs and/or GPUs. Specifically, processor(s) 808 are programmed to execute computer-executable instructions for implementing aspects of the disclosure. The instructions may be performed by the processor, by multiple processors within computing device 800, or by a processor external to client computing device 800. In some examples, processor(s) 808 are programmed to execute instructions such as those illustrated in the in the accompanying drawings. Moreover, in some examples, processor(s) 808 represent an implementation of analog techniques to perform the operations described herein. For example, the operations may be performed by an analog client computing device 800 and/or a digital client computing device 800. Presentation component(s) 810 present data indications to a user or other device. Exemplary presentation components include a display device, speaker, printing component, vibrating component, etc. One skilled in the art will understand and appreciate that computer data may be presented in a number of ways, such as visually in a graphical user interface (GUI), audibly through speakers, wirelessly between computing devices 800, across a wired connection, or in other ways. I/O ports 814 allow computing device 800 to be logically coupled to other devices including I/O components 816, some of which may be built in. Example I/O components 816 include, for example but without limitation, a microphone, joystick, game pad, satellite dish, scanner, printer, wireless device, etc.

Computing device 800 may operate in a networked environment via network component 812 using logical connections to one or more remote computers. In some examples, network component 812 includes a network interface card and/or computer-executable instructions (e.g., a driver) for operating the network interface card. Communication between computing device 800 and other devices may occur using any protocol or mechanism over any wired or wireless connection. In some examples, network component 812 is operable to communicate data over public, private, or hybrid (public and private) using a transfer protocol, between devices wirelessly using short range communication technologies (e.g., near-field communication (NFC), Bluetooth™ branded communications, or the like), or a combination thereof. Network component 812 communicates over wireless communication link 822 and/or a wired communication link 822 *a* to a cloud resource 824 across network 826. Various different examples of communication links 822 and 822 *a* include a wireless connection, a wired connection, and/or a dedicated link, and in some examples, at least a portion is routed through the internet.

Although described in connection with an example computing device 800, examples of the disclosure are capable of implementation with numerous other general-purpose or special-purpose computing system environments, configurations, or devices. Examples of well-known computing systems, environments, and/or configurations that may be suitable for use with aspects of the disclosure include, but are not limited to, smart phones, mobile tablets, mobile computing devices, personal computers, server computers, hand-held or laptop devices, multiprocessor systems, gaming consoles, microprocessor-based systems, set top boxes, programmable consumer electronics, mobile telephones, mobile computing and/or communication devices in wearable or accessory form factors (e.g., watches, glasses, headsets, or earphones), network PCs, minicomputers, mainframe computers, distributed computing environments that include any of the above systems or devices, virtual reality (VR) devices, augmented reality (AR) devices, mixed reality devices, holographic device, and the like. Such systems or devices may accept input from the user in any way, including from input devices such as a keyboard or pointing device, via gesture input, proximity input (such as by hovering), and/or via voice input.

Examples of the disclosure may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other examples of the disclosure may include different computer-executable instructions or components having more or less functionality than illustrated and described herein. In examples involving a general-purpose computer, aspects of the disclosure transform the general-purpose computer into a special-purpose computing device when configured to execute the instructions described herein.

By way of example and not limitation, computer readable media comprise computer storage media and communication media. Computer storage media include volatile and nonvolatile, removable and non-removable memory implemented in any method or technology for storage of information such as computer readable instructions, data structures, program modules, or the like. Computer storage media are tangible and mutually exclusive to communication media. Computer storage media are implemented in hardware and are non-transitory, i.e., exclude carrier waves and propagated signals. Computer storage media for purposes of this disclosure are not signals per se. Exemplary computer storage media include hard disks, flash drives, solid-state memory, phase change random-access memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium that may be used to store information for access by a computing device. In contrast, communication media typically embody computer readable instructions, data structures, program modules, or the like in a modulated data signal such as a carrier wave or other transport mechanism and include any information delivery media.

In some examples, a computer-implemented method includes generating a plurality of clusters; generating, for a new user, a profile; associating the generated profile into a cluster of the plurality of clusters; and generating, by a machine learning (ML) model, a recommendation for the user based on the associated cluster.

In some examples, an apparatus includes a user interface (UI); a memory; and a processor coupled to the memory configured to: control the UI to present a questionnaire; receive, via the UI, a response to the questionnaire; generate a profile associated with the user based on the received responses to the questionnaire and the captured facial scan; associate the generated profile into a cluster of a plurality of clusters; and execute a machine learning (ML) model to generate a recommendation for the user based on the associated cluster.

In some examples, a computer-readable storage media stores instructions that, when executed by a processor, cause the processor to generate a plurality of clusters, each cluster of the generated plurality of clusters including at least a stage of menopause and symptoms experienced related to menopause; generate, for a new user, a profile, the generated profile including at least an identified user stage of menopause and user symptoms experienced related to menopause; associate the generated profile into a cluster of the plurality of clusters; and generating, by a machine learning (ML) model, a recommendation for the user based on the associated cluster.

Further examples for generating a recommendation for a user are described herein.

Various examples further include one or more of the following:

- wherein generating the plurality of clusters further comprises: identifying a plurality of existing profiles, each existing profile of the plurality of existing profiles including a set of variables; for each of the existing profiles, identifying a value for each variable of the set of variables; and determining, by a clustering algorithm, a first existing profile and a second existing profile, of the plurality of existing profiles, have a similarity above a similarity threshold; and generating, by the clustering algorithm, the cluster including the first existing profile and the second existing profile;
- wherein associating the generated profile into the cluster of the plurality of clusters further comprises: identifying a set of variables for the generated profile; identifying a value for each variable of the set of variables for the generated profile; based on the identified value for each variable of the set of variables for the generated profile, determining, by the clustering algorithm, the cluster of the plurality of clusters most similar to the generated profile; and associating the generated profile into the determined cluster;
- wherein the set of variables include variables related to at least one of age, number of symptoms, types of symptoms, severity of symptoms, ethnicity, income, geographical location, or awareness of menopause;
- wherein generating the recommendation for the user further comprises: determining a health outcome associated with the cluster of the plurality of clusters; identifying an intervention that, when applied, has a likelihood of addressing the determined health outcome; and generating, by the ML model, the recommendation for the user, the recommendation including the intervention;
- wherein: the determined health outcome is a stage of menopause; and the identified intervention includes at least one of a treatment for a symptom of the stage of menopause or educational content associated with the stage of menopause;
- further comprising: receiving feedback indicating a result of the recommendation; and based on the received feedback, updating the ML model;
- further comprising: receiving updated information from the new user; based on the received updated information, associating the generated profile into a second cluster of the plurality of clusters, the second cluster different than the cluster; and generating, by the ML model, a second recommendation for the user based on the associated second cluster;
- determine a health outcome associated with the cluster of the plurality of clusters, the determined health outcome including the user identified stage of menopause; identify an intervention associated with the associated cluster that, when applied, has a likelihood of addressing the determined health outcome, the identified intervention including at least one of a treatment for a symptom of the stage of menopause or educational content associated with the stage of menopause; and generating, by the ML model, the recommendation for the user, the recommendation including the intervention The order of execution or performance of the operations in examples of the disclosure illustrated and described herein is not essential, and may be performed in different sequential manners in various examples. For example, it is contemplated that executing or performing a particular operation before, contemporaneously with, or after another operation is within the scope of aspects of the disclosure. When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of" The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A computer-implemented method, comprising:

presenting, on a user interface (UI), a questionnaire;

receiving, on the UI, one or more responses to the questionnaire, the received one or more responses including a goal of a new user, the goal associated with a health outcome, wherein the health outcome is a stage of menopause;

generating a plurality of clusters of a plurality of existing profiles having a similarity above a similarity threshold, wherein generating the plurality of clusters includes (i) performing a hierarchical feature collapse and (ii) selecting top features by performing a principal component analysis (PCA) to group profile features together to determine strength of similarity between the profile features, and wherein the profile features include both behavioral features and biological features;

generating, for the new user, a profile;

associating the generated profile into a cluster of the plurality of clusters based on the similarity for the generated profile being above the similarity threshold;

determining a persona for the cluster of the plurality of clusters, wherein the determined persona is an artificial profile representing one or more data values of the generated profile in the cluster;

storing, in a specialized data structure, the cluster together with the determined persona for the cluster;

for the associated cluster, identifying, in the specialized data structure, a highest ranked intervention for the health outcome for the determined persona; and generating, by a machine learning (ML) model, a recommendation for the new user based on the associated cluster and the determined persona, wherein the generated recommendation includes the identified highest ranked intervention that, when applied, has a likelihood of accomplishing the goal associated with addressing the health outcome.

2. The computer-implemented method of claim 1, wherein generating the plurality of clusters further comprises:

identifying the plurality of existing profiles, each existing profile of the plurality of existing profiles including a set of variables;

for each of the existing profiles, identifying a value for each variable of the set of variables;

determining, by a clustering algorithm, a first existing profile and a second existing profile, of the plurality of existing profiles, have a similarity above the similarity threshold; and generating, by the clustering algorithm, the cluster including the first existing profile and the second existing profile.

3. The computer-implemented method of claim 2, wherein associating the generated profile into the cluster of the plurality of clusters further comprises:

identifying a new set of variables for the generated profile;

identifying a value for each variable of the new set of variables for the generated profile;

based on the identified value for each variable of the new set of variables for the generated profile, determining, by the clustering algorithm, the cluster of the plurality of clusters most similar to the generated profile; and associating the generated profile into the determined cluster.

4. The computer-implemented method of claim 3, wherein the set of variables include variables related to at least one of age, number of symptoms, types of symptoms, severity of symptoms, ethnicity, income, geographical location, or awareness of menopause.

5. The computer-implemented method of claim 1, wherein generating the recommendation for the user further comprises:

determining the health outcome associated with the cluster of the plurality of clusters;

identifying the intervention that, when applied, has a likelihood of addressing the determined health outcome, wherein the identified intervention includes at least one of a treatment for a symptom of the stage of menopause or educational content associated with the stage of menopause; and generating, by the ML model, the recommendation for the user, the recommendation including the intervention.

6. The computer-implemented method of claim 1, further comprising:

determining prior consent for named customer data is received;

capturing both anonymous data and the named customer data via user navigation and input context on the UI;

storing the captured anonymous data and the named customer data in the specialized data structure; and training a second ML model to associate the generated profile for the new user into the cluster based on the captured anonymous data and the named customer data.

7. The computer-implemented method of claim 1, further comprising:

receiving feedback indicating a result of the recommendation; and based on the received feedback, updating the ML model.

8. The computer-implemented method of claim 1, further comprising:

receiving updated information from the new user;

based on the received updated information, associating the generated profile into a second cluster of the plurality of clusters, the second cluster different than the cluster; and generating, by the ML model, a second recommendation for the user based on the associated second cluster.

9. An apparatus comprising:

a user interface (UI) configured to present a questionnaire;

a memory configured to store a specialized data structure; and a processor coupled to the memory configured to:

receive, via the UI, one or more responses to the questionnaire, the received one or more responses including a goal of a new user, the goal associated with a health outcome, wherein the health outcome is a stage of menopause;

generate a plurality of clusters of a plurality of existing profiles having a similarity above a similarity threshold, wherein generating the plurality of clusters includes (i) performing a hierarchical feature collapse and (ii) selecting top features by performing a principal component analysis (PCA) to group profile features together to determine strength of similarity between the profile features, and wherein the profile features include both behavioral features and biological features;

generate, for the new user, a profile associated with the user based on the received responses to the questionnaire;

associate the generated profile into a cluster of a plurality of clusters based on the similarity for the generated profile being above the similarity threshold;

determine a persona for the cluster of the plurality of clusters, wherein the determined persona is an artificial profile representing one or more data values of the generated profile in the cluster;

store, in the specialized data structure, the cluster together with the determined persona for the cluster;

for the associated cluster, identifying, in the specialized data structure, a highest ranked intervention for the health outcome for the determined persona; and execute a machine learning (ML) model to generate a recommendation for the new user based on the associated cluster and the determined persona, wherein the generated recommendation includes the identified highest ranked intervention that, when applied, has a likelihood of accomplishing the goal associated with addressing the health outcome.

10. The apparatus of claim 9, wherein the processor is further configured to:

identify the plurality of existing profiles, each existing profile of the plurality of existing profiles including a set of variables;

for each of the existing profiles, identify a value for each variable of the set of variables;

execute a clustering algorithm to determine a first existing profile and a second existing profile, of the plurality of existing profiles, have a similarity above the similarity threshold; and generate, by the clustering algorithm, the cluster including the first existing profile and the second existing profile.

11. The apparatus of claim 10, wherein, to associate the generated profile into the cluster of the plurality of clusters, the processor is further configured to:

identify a new set of variables for the generated profile;

identify a value for each variable of the new set of variables for the generated profile;

based on the identified value for each variable of the new set of variables for the generated profile, execute the clustering algorithm to determine the cluster of the plurality of clusters most similar to the generated profile; and associate the generated profile into the determined cluster.

12. The apparatus of claim 11, wherein the set of variables include variables related to at least one of age, number of symptoms, types of symptoms, severity of symptoms, ethnicity, income, geographical location, or awareness of menopause.

13. The apparatus of claim 9, wherein, to generate the recommendation for the user, the processor is further configured to:

determine the health outcome associated with the cluster of the plurality of clusters;

identify the intervention that, when applied, has a likelihood of addressing the determined health outcome; and execute the ML model to generate the recommendation for the user, the recommendation including the intervention.

14. The apparatus of claim 13, wherein:

the identified intervention includes at least one of a treatment for a symptom of the stage of menopause or educational content associated with the stage of menopause.

15. The apparatus of claim 9, wherein the processor is further configured to:

receive updated information from the new user;

based on the received updated information, associate the generated profile into a second cluster of the plurality of clusters, the second cluster different than the cluster; and execute the ML model to generate a second recommendation for the user based on the associated second cluster.

16. One or more non-transitory computer readable media storing instructions that, when executed by a processor, cause the processor to:

generate a plurality of clusters, each cluster of the generated plurality of clusters including at least a stage of menopause and symptoms experienced related to menopause, wherein generating the plurality of clusters includes (i) performing a hierarchical feature collapse and (ii) selecting top features by performing a principal component analysis (PCA) to group profile features together to determine strength of similarity between the profile features, and wherein the profile features include both behavioral features and biological features;

determine a persona for each of the generated clusters, wherein the determined persona is an artificial profile representing one or more data values of a generated profile in the cluster;

store, in a specialized data structure, each of the generated clusters together with the determined persona for the cluster;

generate, for a new user, a profile based on one or more responses to a questionnaire, the generated profile including at least an identified user stage of menopause and user symptoms experienced related to menopause, wherein the one or more responses include a goal of the new user;

associate the generated profile into a cluster of the plurality of clusters; and generate, by a machine learning (ML) model, a recommendation for the user based on the associated cluster and the determined persona, wherein the generated recommendation includes an intervention that, when applied, has a likelihood of accomplishing the goal associated with addressing the identified user stage of menopause.

17. The one or more non-transitory computer readable media of claim 16, further storing instructions for generating the recommendation for the user that, when executed by the processor, cause the processor to:

identify an intervention associated with the associated cluster that, when applied, has a likelihood of addressing the identified user stage of menopause, the identified intervention including at least one of a treatment for a symptom of the stage of menopause or educational content associated with the stage of menopause; and generating, by the ML model, the recommendation for the user, the recommendation including the intervention.

18. The one or more non-transitory computer readable media of claim 16, further storing instructions for generating the plurality of clusters that, when executed by the processor, cause the processor to:

identify a plurality of existing profiles, each existing profile of the plurality of existing profiles including a set of variables;

for each of the existing profiles, identify a value for each variable of the set of variables;

determine, by a clustering algorithm, a first existing profile and a second existing profile, of the plurality of existing profiles, have a similarity above a similarity threshold; and generate, by the clustering algorithm, the cluster including the first existing profile and the second existing profile.

19. The one or more non-transitory computer readable media of claim 18, further storing instructions for associating the generated profile into the cluster of the plurality of clusters that, when executed by the processor, cause the processor to:

identify a new set of variables for the generated profile;

identify a value for each variable of the new set of variables for the generated profile;

based on the identified value for each variable of the new set of variables for the generated profile, determine, by the clustering algorithm, the cluster of the plurality of clusters most similar to the generated profile; and associate the generated profile into the determined cluster.

20. The one or more non-transitory computer readable media of claim 16, further storing instructions that, when executed by the processor, cause the processor to:

receive updated information from the new user;

based on the received updated information, associate the generated profile into a second cluster of the plurality of clusters, the second cluster different than the cluster; and generate, by the ML model, a second recommendation for the user based on the associated second cluster.

* * * * *